(12) United States Patent
Rychak et al.

(10) Patent No.: US 11,766,243 B2
(45) Date of Patent: Sep. 26, 2023

(54) COMPOSITION AND METHODS FOR SENSITIVE MOLECULAR ANALYSIS

(71) Applicants: TRUST BIO-SONICS, INC., Hsinchu County (TW); Joshua Rychak, Oceanside, CA (US)

(72) Inventors: Joshua Rychak, Oceanside, CA (US); Shih-Tsung Kang, New Taipei (TW); ChungHsin Wang, Taipei (TW)

(73) Assignee: Trust Bio-Sonics, Inc., Hsinchu County (TW)

( * ) Notice: Subject to any disclaimer, the term of this patent is extended or adjusted under 35 U.S.C. 154(b) by 266 days.

(21) Appl. No.: 16/980,416

(22) PCT Filed: Mar. 13, 2019

(86) PCT No.: PCT/IB2019/000242
§ 371 (c)(1),
(2) Date: Sep. 13, 2020

(87) PCT Pub. No.: WO2019/175664
PCT Pub. Date: Sep. 19, 2019

(65) Prior Publication Data
US 2021/0000448 A1 Jan. 7, 2021

Related U.S. Application Data

(60) Provisional application No. 62/642,017, filed on Mar. 13, 2018.

(51) Int. Cl.
*A61B 8/08* (2006.01)
*G16H 50/30* (2018.01)
(Continued)

(52) U.S. Cl.
CPC .............. *A61B 8/481* (2013.01); *A61B 8/085* (2013.01); *A61B 8/0883* (2013.01); *A61B 8/461* (2013.01);
(Continued)

(58) Field of Classification Search
CPC ....... A61B 8/481; A61B 8/085; A61B 8/0883; A61B 8/461; G16H 50/30; A61K 49/221; A61K 49/223
See application file for complete search history.

(56) References Cited

U.S. PATENT DOCUMENTS

2006/0161062 A1\* 7/2006 Arditi ...................... A61B 8/13
600/443
2017/0196539 A1\* 7/2017 Gu ........................ A61B 8/481
(Continued)

FOREIGN PATENT DOCUMENTS

CN 104939806 A 9/2015
WO WO-2013104726 A1 \* 7/2013 ............. A61B 8/481

*Primary Examiner* — John Denny Li

(57) ABSTRACT

A method for ascertaining the presence of target-bound microbubbles in the context of ultrasound molecular imaging is taught. This method, referred to herein as dynamic scaling ultrasound molecular imaging, relies upon the time-varying behavior contrast agents within a region expressing a molecular imaging target and that within a reference region. Ultrasound contrast agents compositions that enable use of the method are also taught. The method is useful for the use of ultrasound molecular imaging in diagnosing and monitoring treatment.

17 Claims, 22 Drawing Sheets

A.

B.

(51) Int. Cl.
*A61B 8/00* (2006.01)
*A61K 49/22* (2006.01)

(52) U.S. Cl.
CPC .......... *A61K 49/221* (2013.01); *A61K 49/223* (2013.01); *G16H 50/30* (2018.01)

(56) References Cited

U.S. PATENT DOCUMENTS

2018/0279995 A1* 10/2018 Doyle .................. A61B 8/4427
2019/0154822 A1* 5/2019 Berlin .................. G01S 15/8979
2019/0192253 A1* 6/2019 Yang ...................... A61B 90/39

* cited by examiner

FIG. 3A/B
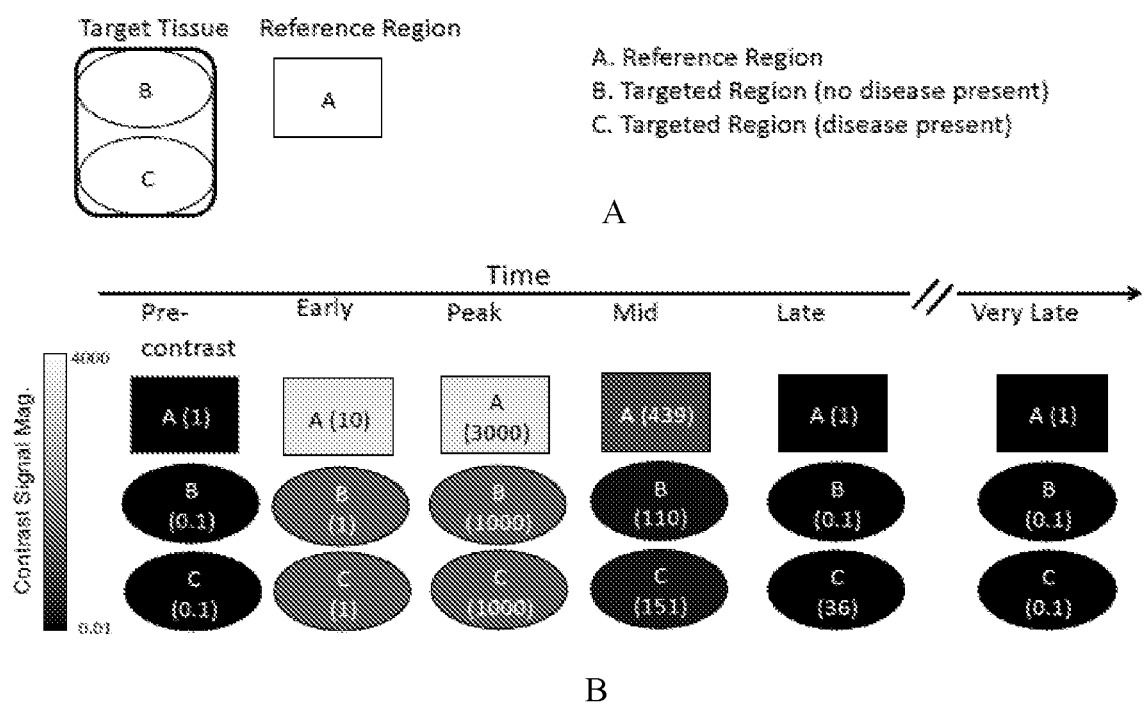

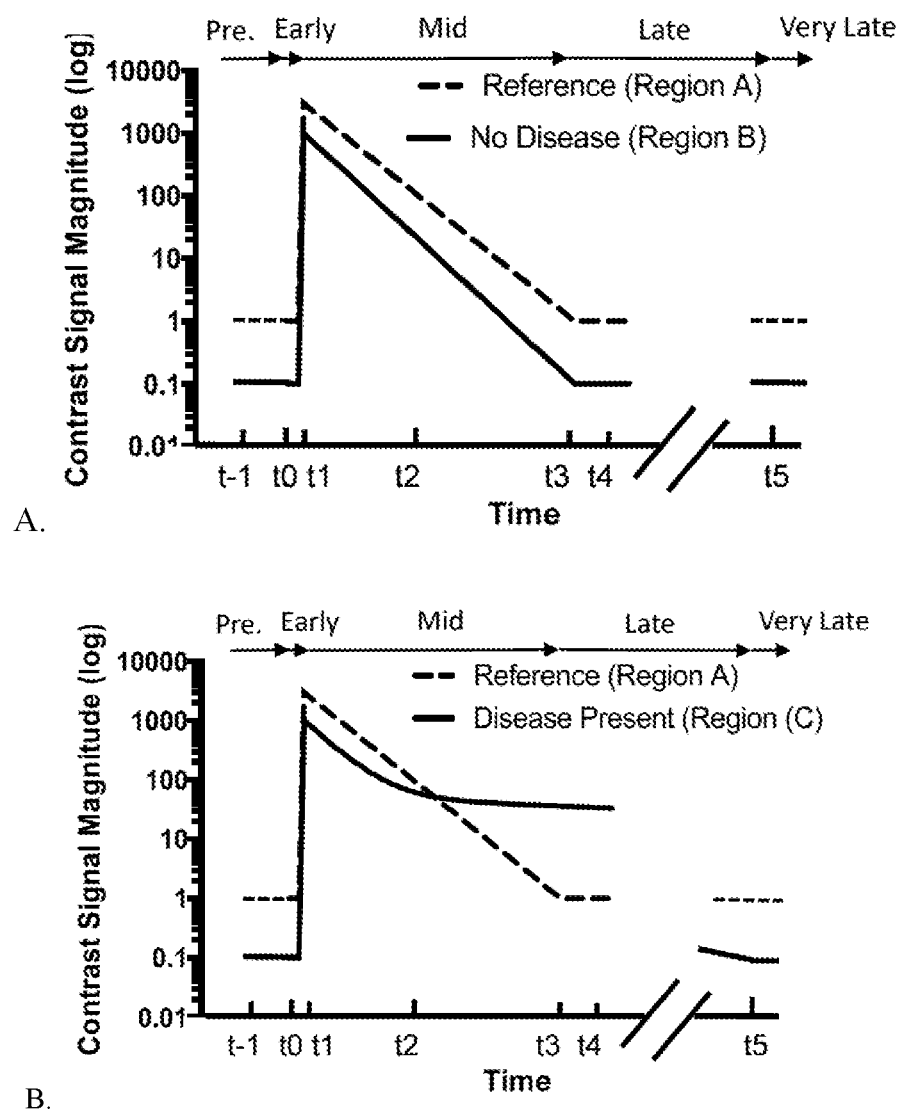
FIG. 4A/B

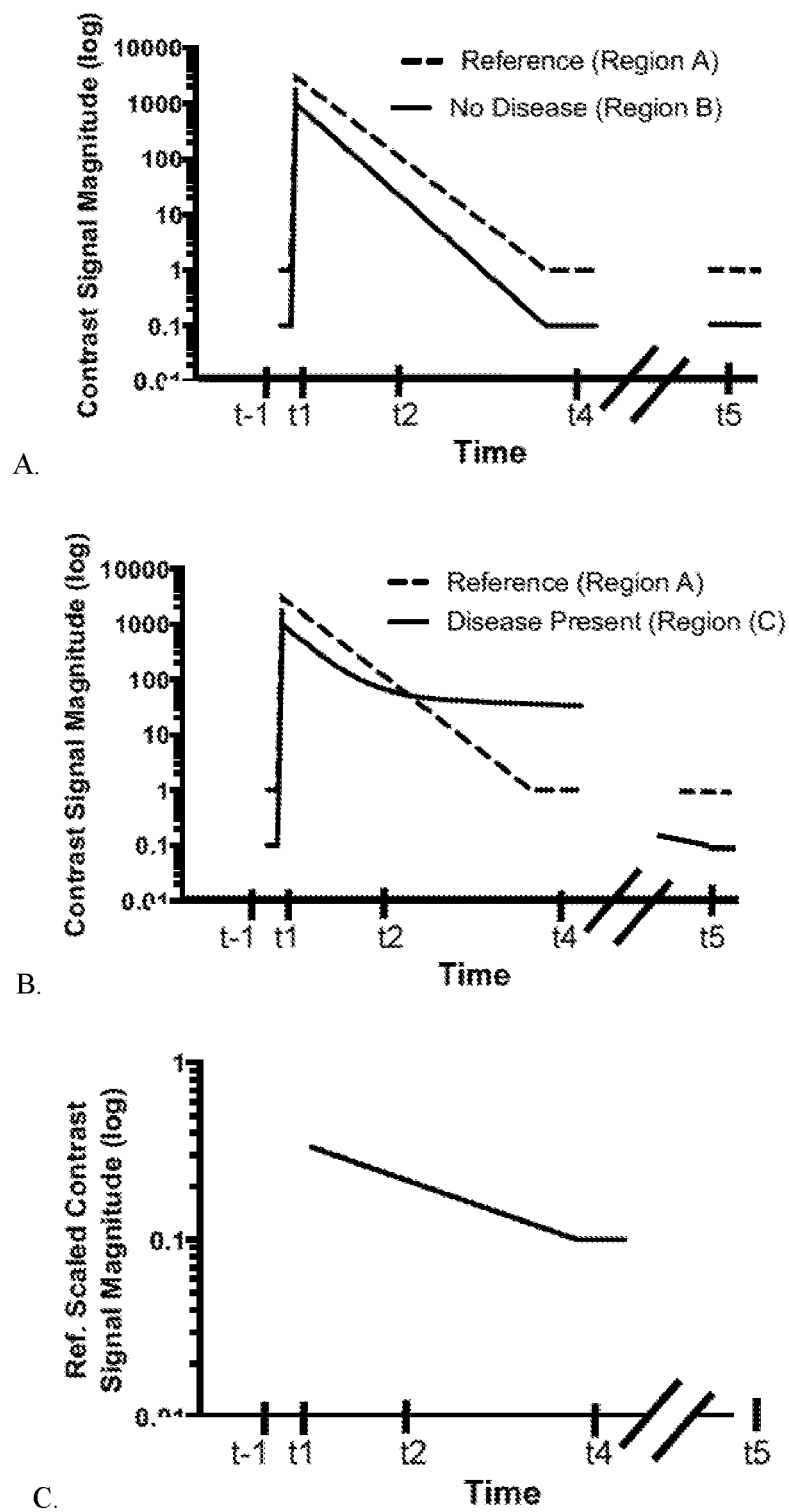
FIG. 5A-C

FIG. 5D-F
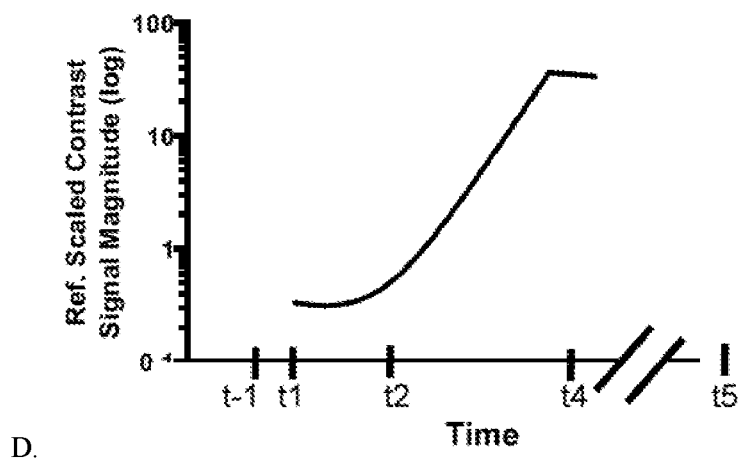
D.
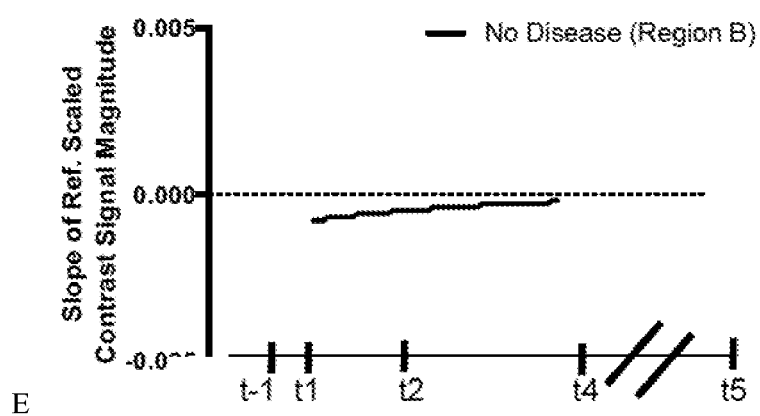
E.
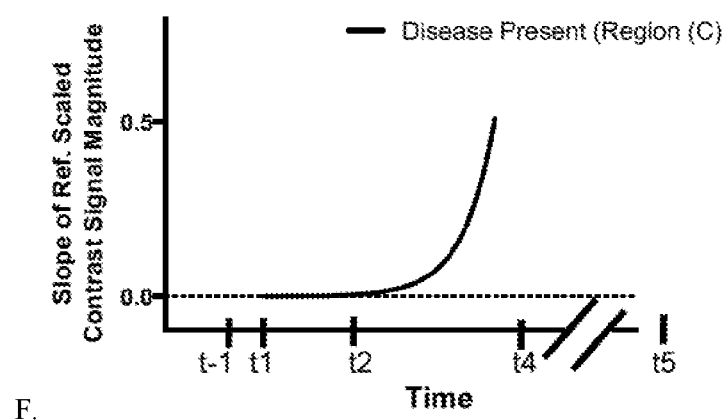
F.

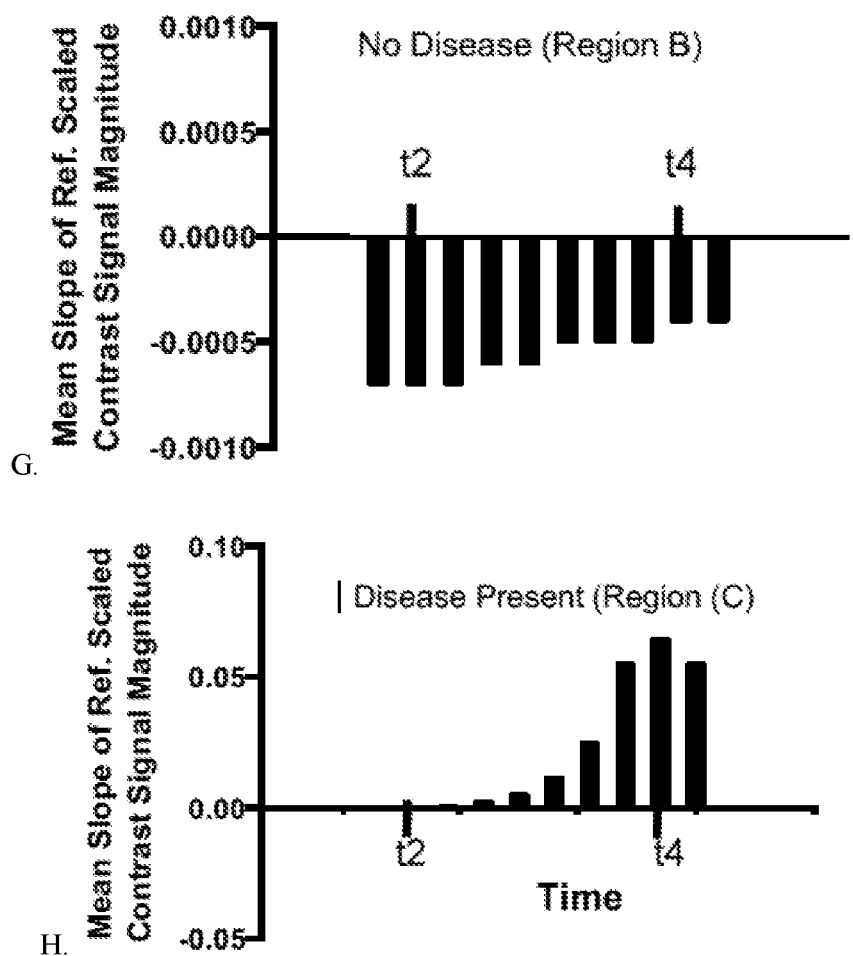
FIG. 5G/H

A. Reference Region
B. Targeted Region (no disease present)
C. Targeted Region (disease present)

FIG. 17A-C
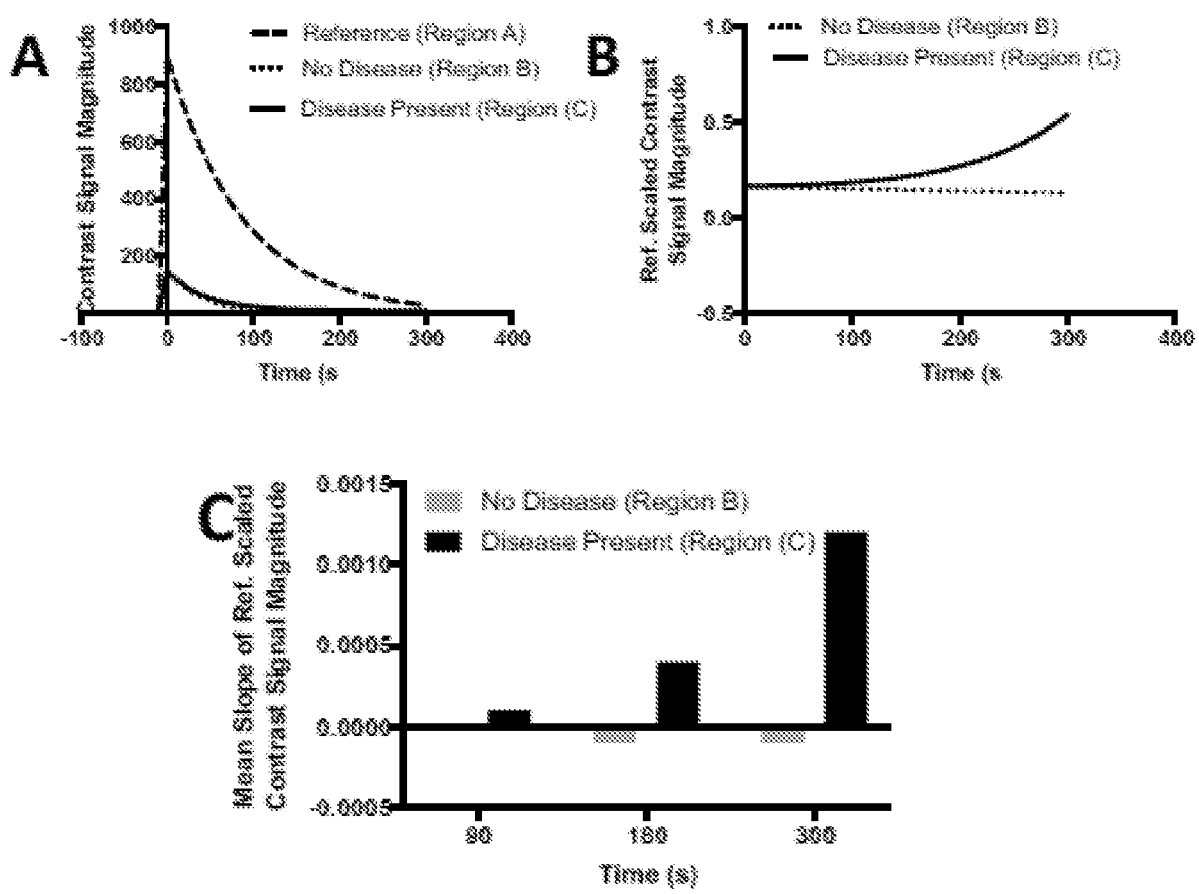

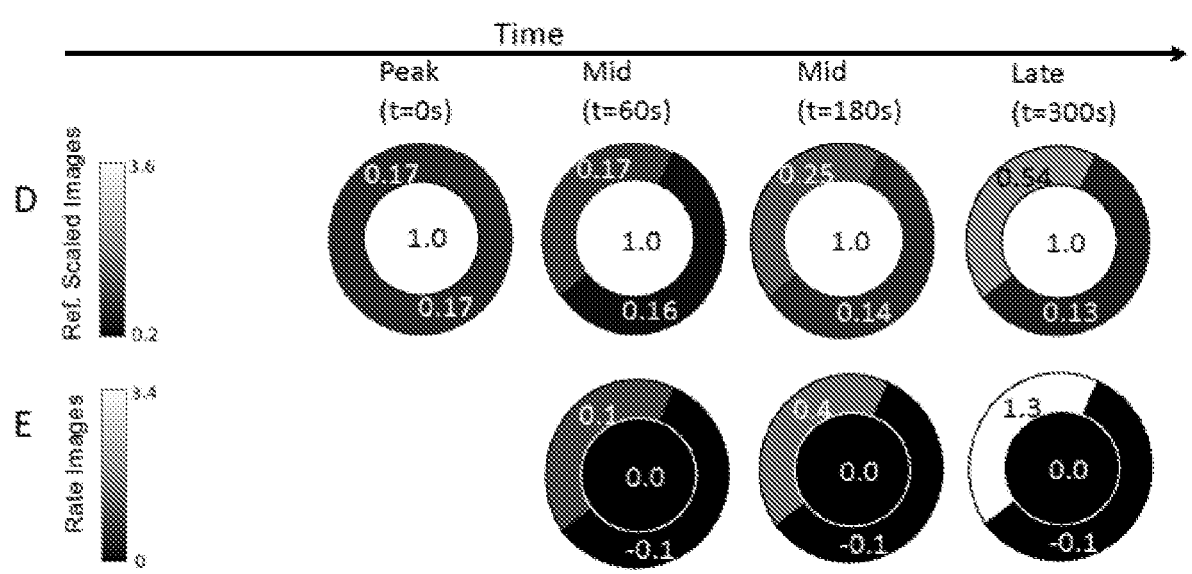
FIG. 17D/E

FIG. 18A-E
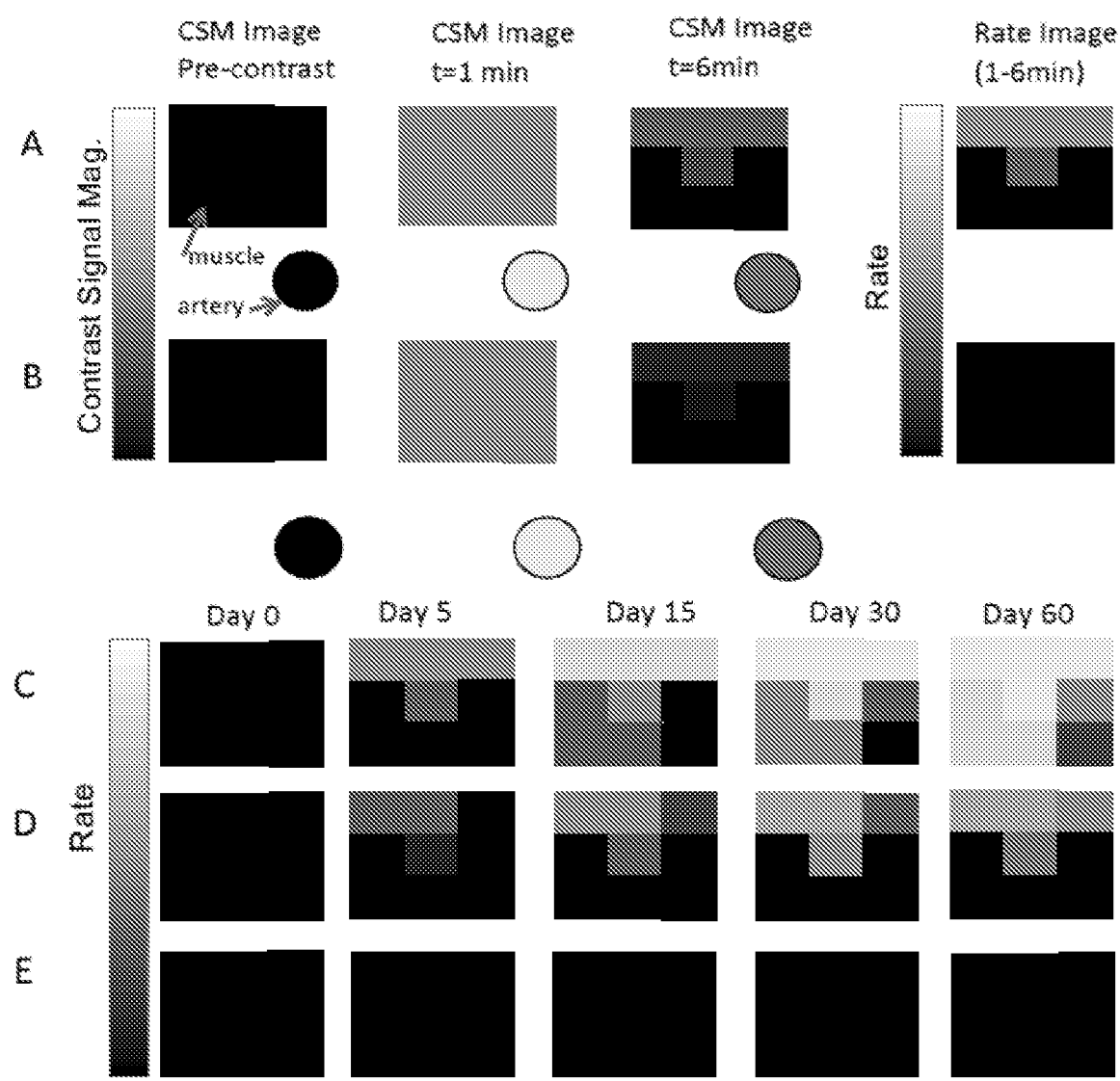

COMPOSITION AND METHODS FOR SENSITIVE MOLECULAR ANALYSIS

BACKGROUND OF THE INVENTION

The use of ultrasound to generate diagnostically useful images is well described in the prior art. Ultrasound imaging can be performed at a high frame rate (up to several tens of frames per second can be routinely achieved), does not entail the use of ionizing radiation, and the equipment is of low cost and high portability relative to other imaging modalities. These characteristics make diagnostic ultrasound imaging useful for evaluating a wide range of disease states and imaging various biological tissues.

SUMMARY OF THE INVENTION

In accordance with the present invention, the present invention provides a method for quantifying magnitude of a contrast signal within a region of interest (ROI) by analyzing a time series of ultrasound molecular images acquired in a dynamic scaling manner, the method comprises administering to a target tissue of a subject a targeted contrast agent (such as microbubbles) to image the presence of targeted molecular markers of disease; selecting a reference region representative of the amount of contrast agent circulating within the blood pool in a dynamic, time-varying manner; imaging said target tissue including the selected reference region; determining the magnitude quantitatively of an area of disease by said dynamic scaling, time-varying manner procedure wherein said targeted contrast agent is configured to be bound to said molecular markers of disease expressed within the diseased region.

In one aspect, said dynamic scaling, time-varying manner procedure comprises
a. providing a time series of images depicting a single field of view,
b. selecting one or more regions of interest and one or more corresponding reference regions,
c. forming a reference-scaled image, and/or a reference-scaled signal magnitude in which the region of interest and reference region are obtained at the same instant in the time series,
d. performing the scaling operation of (c) on two or more images in the time series to determine the time-intensity relationship of the reference-scaled magnitude quantitatively; wherein the reference-scaled signal increases in the diseased region and decreases in the non-diseased region.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A/B provides one embodiment of a general example of ultrasound molecular imaging in accordance with the practice of the present invention. The target tissue is composed of two regions: Region B (in which the disease of interest is not present) and Region C (in which the disease is present). A third region (A) serves as a reference region. The bottom panel 3B depicts representative images for each region acquired at various timepoints during the imaging session. The pixel intensity (here depicted in shades of grey) corresponds to the contrast signal magnitude. The numbers in each region represent the contrast signal magnitude at the given timepoint.

FIG. 4A/B. shows the exemplary Time-Intensity Curves corresponding to the simplified illustrations of FIG. 3B. (4A) Contrast signal magnitude is plotted as a function of time for Region B (no disease present) and Region A (the reference region). (4B) Contrast signal magnitude as a function of time for Region C (disease present) and Region A (reference region). Note break in time axis scale between t4 and t5.

FIG. 5A-H shows dynamic scaling curves corresponding to the data of FIGS. 3-4. The contrast signal magnitude versus time curves of FIG. 3B are shown in (5A) and (5B). The reference-scaled contrast signal magnitude over time is shown for (5C) the non-diseased region and (5D) the diseased region. The instantaneous slope of the reference-scaled contrast signal magnitude over time is shown for the (5E) non-diseased region and (5F) diseased region. The average slope of the reference-scaled contrast signal magnitude between t1 and subsequent time points for the (5G) non-diseased and (5H) diseased region.

FIG. 17A-E. illustrates the dynamic scaling curves corresponding to the data of FIG. 16. (17A) contrast signal magnitude versus time curves (17B) The reference-scaled contrast signal magnitude over time, and (17C) average slope of the reference-scaled contrast signal magnitude between t=60 s and 90, 180, and 300 s. Reference-scaled images are shown in (17D) and corresponding rate images are shown in (17E).

FIG. 18A-E provides yet another embodiment of a method re monitoring response to therapy by dynamic scaling ultrasound molecular imaging. A time series of simplified contrast signal magnitude images within a region of muscle (target region) and adjacent artery (reference region) for (18A) a patient exhibiting a positive therapeutic response and (18B) a patient exhibiting a negative response. Rate images corresponding to the contrast signal magnitude series are shown at the far right for each patient. Rate images obtained by dynamic scaling ultrasound molecular imaging performed at various days during treatment for (18C) a patient exhibiting a strong response, (18D) a patient exhibiting an intermediate response, and (18E) a patient exhibiting a poor response.

DETAILED DESCRIPTION OF THE INVENTION

Figure 1:
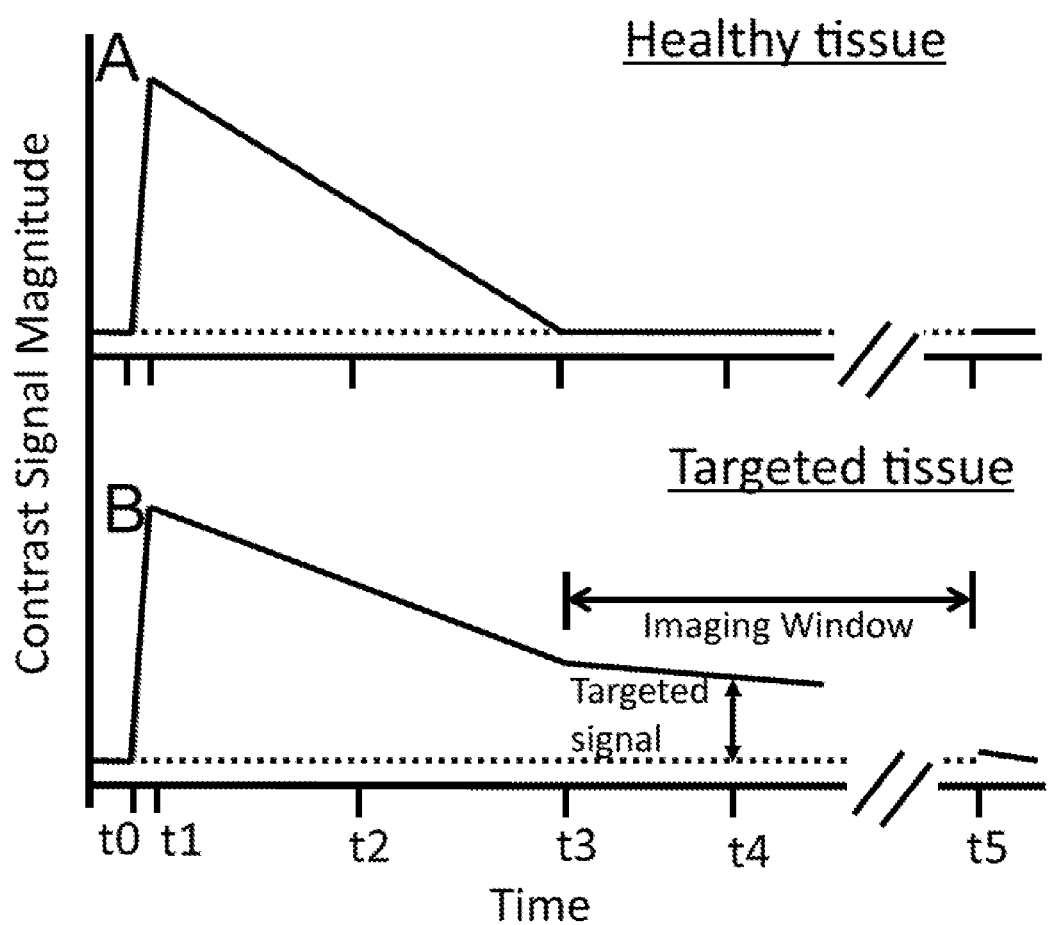
FIG. 1A/B shows simplified time-intensity curves depicting behavior of a targeted microbubble using non-destructive imaging. Two regions of interest are shown: (1A) one in which the imaging target is not expressed (healthy tissue) and (1B) one in which the imaging target is expressed (targeted tissue). The late-phase imaging window is noted on the bottom curve, as is the magnitude of the target-bound microbubble signal at t4.

The use of contrast agents (microbubbles and related compositions) extends the utility of ultrasound imaging. Two classes of ultrasound contrast agents are widely used: 1) non-targeted, which are primarily used for imaging blood flow and border detection, and 2) targeted, which are generally used for molecular imaging. In both cases, a biocompatible gas serves as the contrast-producing substance. The gas phase is typically encapsulated by a shell, which stabilizes the gas and imparts desirable pharmacokinetic and pharmacodynamic properties. In the case of targeted contrast agents, the shell is formulated with a substance able to mediate retention of the contrast agent to a specific molecule or cell type. Representative non-targeted microbubbles are described, for example, in the references of Table 1. Representative targeted microbubbles are described, for example, in U.S. Ser. No. 08/958,993 (Klaveness et al) and U.S. Ser. No. 14/639,055 (Rychak et al). These and all other referenced patents, applications, and publications are incorporated herein by reference in their entirety.

TABLE 1

Physical characteristics of ultrasound contrast agents used in the field.

| Agent (Manufacturer) | Mean Diameter | Size Range | Shell | Reference |
|---|---|---|---|---|
| Definity (Lantheus) | 1.1-3.3 | 2% greater than 10 um | Phospholipid | Prescribing information |
| Optison (GE) | 2.0-4.5 | 7% greater than 10 um | Human protein | Podell et al, 1999 |
| Sonovue (Bracco) | 2.5 | 10% greater than 8 um | Phospholipid | Schneider et al, 1999 |
| Imagent | 6 um | 0.2% greater | Phospholipid | Prescribing |

TABLE 1-continued

Physical characteristics of ultrasound contrast agents used in the field.

| Agent (Manufacturer) | Mean Diameter | Size Range | Shell | Reference |
|---|---|---|---|---|
| (Imcor) Sonazoid (Daiichi) | 2.1 +/− 0.1 | than 10 um 0.05% +/− 1 greater than 7 um | Phospholipid | Information Sontum, 2008 |

Several contrast agent characteristics are important to consider in the context of the present invention. Microbubbles are generally polydisperse, with diameters ranging from approximately 1 to 20 um. A wide size distribution is advantageous in some settings, as this facilitates imaging over a wide range of imaging frequencies and tissue depths. The utility efficacy with which a microbubble generates an ultrasound contrast signal reportedly scales with size, and small (diameter 2.0 um and below) microbubbles are generally disfavored for ultrasound imaging (Sontum et al, 1999; Gorce et al, 2000). Essentially all commercially available microbubble products for human use have a mean diameter above 2 um.

Essentially monodisperse microbubbles have been reported in the literature, for example Feshiten et al (2009). Such formulations may have advantages in niche applications, for example ultra-high frequency imaging in small animals, but are generally not desirable for use in clinical applications due to the low imaging frequencies required.

For targeted microbubbles, the conjugation of a targeting ligand to the shell is of high relevance. Targeting ligands are desired to be biocompatible and to mediate specific and firm attachment of the microbubble to the target molecule or cell. Antibodies, fusion proteins, peptides, nucleic acids, carbohydrates, and polymers have been utilized as targeting ligands.

Targeted microbubbles are typically administered as a bolus by intravenous injection. In some cases, intra-arterial administration may be utilized.

Contrast Imaging with Ultrasound

The mechanism by which microbubbles can be used to form a contrast-enhanced ultrasound image has been well described (see, for example, Vannan and Kuersten, 2000). Briefly, microbubbles within the imaged volume are first stimulated with incident ultrasound energy produced by the ultrasound transducer. This stimulation causes a mechanical activation of the microbubbles, often referred to as an oscillation. This activation in turn generates a second acoustic signal, referred to as an echo. The magnitude of the echo signal is proportional to the concentration of activated microbubbles within the imaged volume. The echo is received by the ultrasound transducer converted to an electronic signal then processed to create an image.

The signals obtained by ultrasound are modified by the instrument before being displayed to the user as an image. These modifications include dynamic range compression (e.g. "log compression"), which is necessary to fit the wide range of received acoustic signals into the range of pixel values able to be presented in a video display monitor. These modifications serve to create a visually appealing presentation while highlighting the salient image features; however, they alter the relationship between microbubble concentration and the displayed pixel intensity.

In the context of the present invention, the term "contrast intensity" is used to refer to the signal as displayed to the user (i.e. after compression and post-processing). The term "contrast signal magnitude" is used to refer to same signal prior to compression and post-processing. It should be noted that contrast signal magnitude, as used herein, is directly proportional to the concentration of microbubbles, while this relationship may be altered for the contrast intensity.

The amplitude and phase of the echo produced by the microbubble are substantially different from those produced by tissue or other biological materials. This enables isolation of the two signals, and generation of an image derived from echoes produced by the contrast agents (the contrast image). Several imaging techniques able to detect microbubble contrast agents are known in the art. Of particular interest for the present invention are methods that operate at low mechanical index (MI), so that microbubbles are not excessively destroyed during the imaging process. The distinction between high- and low-MI imaging techniques is reviewed in Porter et al (2014). Exemplary non-destructive contrast imaging methods are power pulse inversion and contrast pulse sequences (CPS). In many cases, the contrast image can be created essentially simultaneously with the image derived from the tissue alone (e.g., the B-mode image), enabling co-registration of the two images. The contrast image may be conveniently presented as an overlay encoded in a color map distinct from that of the tissue image. Moreover, the contrast signal may be presented in linearized units, as taught in U.S. Ser. No. 12/084,934 (Frinking et al). This serves to maintain the proportionality between microbubble concentration and displayed signal intensity, which is altered by compression and post-processing.

Detection of Target-Bound Microbubbles

A challenge in use of targeted microbubbles for ultrasound molecular imaging is that the contrast signals arising from target-bound microbubbles are not readily distinguishable from those arising from microbubbles passing through the imaging region of interest. That is, the contrast signal magnitude produced by a stationary microbubble is essentially identical to that produced by a moving microbubble when displayed on a typical contrast ultrasound image. The signal generated by the target-bound microbubbles comprise the signal of interest in a molecular imaging study, and the identification of target-bound microbubble is therefore of high importance.

The problem of identifying target-bound microbubbles is exacerbated for sparsely expressed molecular targets. In this case, the number of target-bound microbubbles may be substantially lower than the number of circulating microbubbles. Exemplary disease states in which the number to targeted microbubbles is expected to be exceptionally low include atherosclerotic plaque, which presents a limited area over which microbubbles may bind. Target molecules expressed in low copy number, such as CD62, are also expected to contribute to exceptionally low targeted microbubble binding.

There is a need for a method by which to unambiguously identify the presence of target-bound microbubbles in an imaging region of interest. Such a method should be robust and amenable to use in a wide range of tissue types, including those with low target expression or a high degree of motion. Several solutions have been proposed, although as will be clear from the subsequent discussion, all have significant deficiencies that make widespread adoption in clinical practice impractical.

Three classes of methods have been described for discriminating targeted from circulating microbubbles: 1. Late-phase imaging, 2. Burst-refill imaging, and 3. Temporal filtration methods. The function of each method will be considered in turn. As will be clear from the following discussion, the methods offered in the art have significant drawbacks that prevent their suitability for widespread use in many clinical imaging contexts.

Imaging in the Late Phase

Late phase imaging is the perhaps the simplest method, and consists essentially of waiting for a sufficient duration of time to elapse since the administration of the contrast agent for circulating (non-target bound) agents to clear from the ROI (the so-called "late phase"). When an image is acquired in the late phase, it is assumed that most or all of the observed contrast signal is due to target-bound contrast agents. This method has been implemented for example in Smeege et al (2017).

The following example illustrates the use of this method and its limitations. The behavior of targeted microbubbles within a region of interest can be understood in the form of a graph relating contrast signal magnitude and time (commonly referred to as a time-intensity curve). FIG. 1 is an illustration of simplified time intensity curves in a hypothetical tissue in which the imaging target is expressed (diseased tissue) and in which it is absent (non-diseased tissue). The baseline (pre-contrast) contrast signal magnitude is depicted with a dotted line.

The time-intensity curve in FIG. 1 can be divided into three phases, which will be discussed further below. 1) Early phase, occurring between t0 and t1; 2) Mid phase, occurring between t1 and t3; and 3) Late phase, occurring between t3 and t5.

Soon after bolus administration of microbubbles, a steep increase in contrast signal magnitude is observed in the early phase. This is due to entrance of microbubbles into the region of interest by blood flow. The observed contrast signal in the early-phase is dominated by circulating microbubbles, and any target-bound microbubbles comprise a small fraction of the total number of microbubbles within the ROI. For this reason, the time intensity curves look similar for diseased and non-diseased tissue during the early phase.

In the mid-phase, contrast signal magnitude decreases due to the clearance of microbubbles from the blood pool. The contrast signal magnitude observed at any instant is due to a combination of targeted and circulating microbubbles. The rate at which microbubbles clear from the blood pool depends upon microbubble dose, route of administration, cardiac status (heart rate, contractility), ventilation status (oxygen saturation, use of supplemental medical oxygen) and other patient-specific factors.

The late phase is defined as the period in which most to substantially all of the circulating microbubbles have been cleared from the blood pool, and any observed contrast signal within the region of interest is due primarily to the presence of target-bound microbubbles. The late phase therefore constitutes, in theory, a convenient temporal imaging window for assessing the region of interest for the presence of targeted microbubbles.

In practice, the contrast signal magnitude from target-bound microbubbles decreases in the late phase and eventually return to the pre-contrast level. This loss in signal is due to the destruction of target-bound microbubbles through gas exchange and other mechanisms (independent of ultrasound-induced microbubble destruction) that compromise the integrity of the microbubble to produce a contrast signal. The rate at which decay in the target-bound signal occurs is not known a priori, and is dependent upon a number of factors including the microbubble composition, location of the region of interest, the local blood gas composition, density of target-bound microbubbles, and microcirculatory conditions. In practice, the decay of the late phase signal is generally slower than that of the mid-phase signal, although the difference between the two regimes may be slight. This makes differentiation of the two phases from a time-intensity curve difficult to impossible, and introduces uncertainty when using this method.

The discussion above illustrates at least one risk in relying upon the late-phase imaging window as a means for inferring the presence of target-bound microbubbles: the contrast signal magnitude decreases with time, and there is a risk of "missing" the imaging window and falsely concluding the absence of disease. This problem is exacerbated in the case of a sparsely-expressed imaging target in which the late-phase signal may be very close to the pre-contrast baseline.

More importantly, the rate at which microbubbles are cleared from the blood pool in the mid-phase is not known a priori, making it difficult in practice to estimate when to initiate imaging so as to capture the late phase. Table 2 summarizes the late phase imaging window utilized in several clinical and animal studies using VEGFR2 as a molecular target. Substantial differences are noted between studies.

In a research setting, this problem is overcome by the use of negative control experiments. For example, the subject is administered a negative control microbubble, for which target-specific retention does not occur at a meaningful degree, and the time point at which the contrast signal magnitude returns to pre-contrast level may be used to define the start of the late phase for a given experimental setting.

In a practical setting, the use of negative controls is generally not possible. Formulating a negative control imaging agent to be used in conjunction with the targeted agent presents unwanted cost and regulatory hurdles. Additionally, it is unlikely that baseline scans (performed in the absence of disease) would be available for most patients in an acute care setting. Additionally, waiting for the late phase to occur introduces potentially unwanted workflow hurdles for an ultrasound exam.

TABLE 2

Exemplary time scales for late-phase imaging of targeted microbubble accumulation.

| Application | Imaging (time after agent administration) | Reference |
| --- | --- | --- |
| VEGFR2 imaging of malignant lesions in prostate (human) | 10 or 30 min | Smeenge et al, Invest Radiol (2017) |
| VEGFR2 imaging of malignant lesions in breast (human) | 13 to 21 min | Willmann et al, J. Clin. Onc (2017) |
| VEGFR2 imaging of malignant lesions in ovary (human) | 13 to 21 min | Willmann et al, J. Clin. Onc (2017) |
| VEGFR2 imaging of subcutaneous tumor (mouse) | 6 minutes | Anderson et al, Invest Radiol (2011). |
| VEGFR2 imaging of subcutaneous tumor (mouse) | 3 minutes | Xuan et al, Molecular Imaging (2009) |
| VEGFR2 imaging of | 4.5 minutes | Wang et al, Mol. Pharm |

TABLE 2-continued

Exemplary time scales for late-phase imaging
of targeted microbubble accumulation.

| Application | Imaging (time after agent administration) | Reference |
|---|---|---|
| subcutaneous tumor (mouse) | | (2017) |
| VEGFR2 imaging of subcutaneous tumor (mouse) | 10 minutes | Byzl et al, Eur Radiol (2017) |

It should be clear from the above discussion that simple late phase imaging alone is not a suitable method for identifying the presence of target-bound microbubbles in the context of molecular imaging, and is insensitive to low concentrations of target-bound microbubbles. A skilled person in the art would readily recognize the use of suitable microbubbles in accordance with the practice of the invention.

Burst-Refill Imaging

The burst-refill method can discriminate target-bound from circulating microbubbles in either the mid- or late-phase after administration. This method entails applying a short-duration (~1 s) high power (generally MI>0.3) ultrasound sequence to "burst" the microbubbles within the field of view. This causes a near-instantaneous elimination of the contrast signal. Non-destructive imaging is then resumed, and any contrast signal observed is assumed to be from circulating microbubbles entering the field of view. By subtracting the post-burst contrast signal magnitude from the pre-burst, the magnitude of the signal due to target-bound microbubbles alone can be derived. This subtraction procedure may be performed on images using digital image processing.

Figure 2:
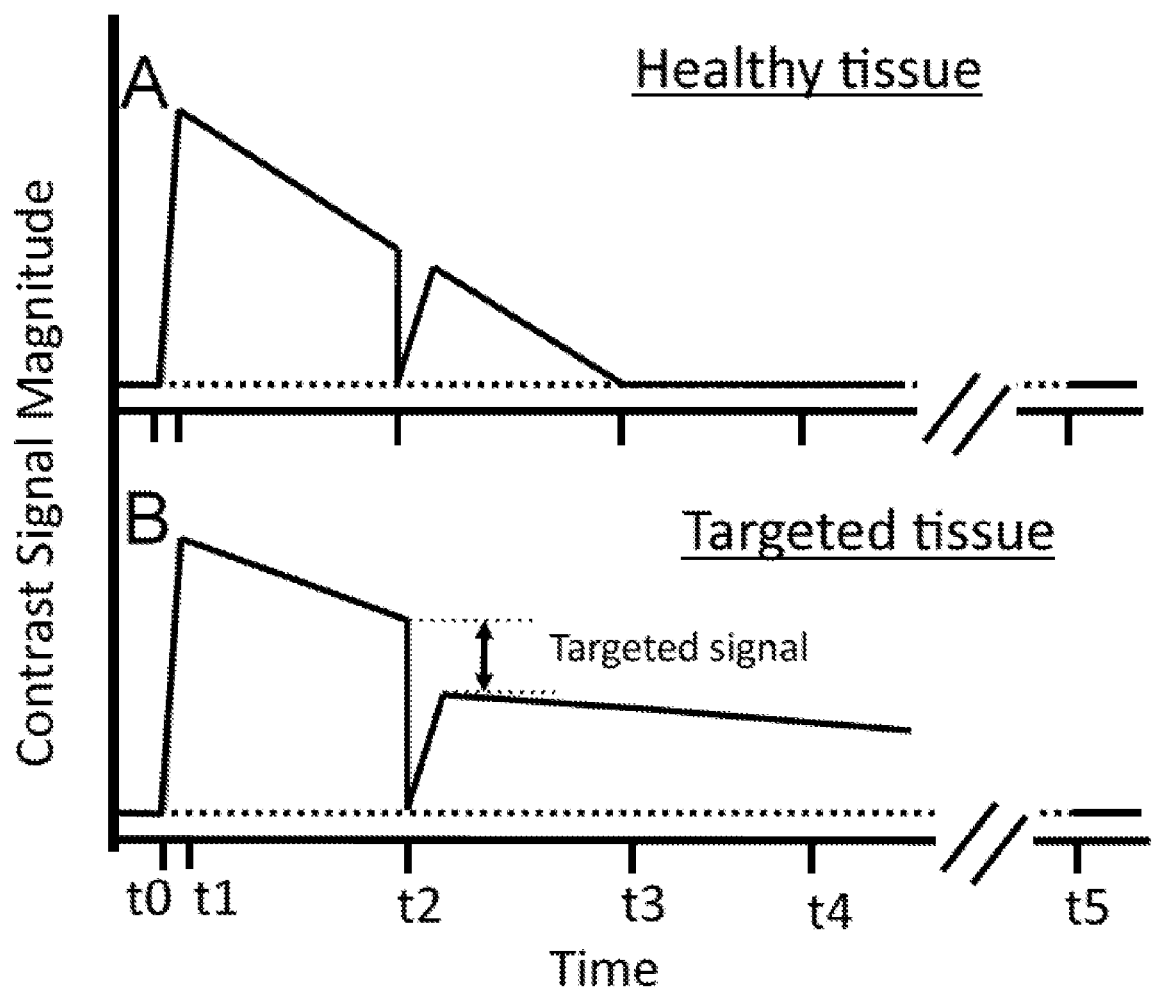
FIG. 2A/B shows simplified time-intensity curves depicting behavior of a targeted microbubble using the burst-refill imaging method. Two regions of interest are shown: (2A) one in which the imaging target is not expressed (healthy tissue) and (2B) one in which the imaging target is expressed (targeted tissue). The destructive burst is performed at t2. The magnitude of the target-bound microbubble signal is noted on the bottom graph.

This method is summarized in the time-intensity curves shown in FIG. 2. In this case, the burst sequence is implemented during the mid-phase (at t2), although it could be implemented during the late phase (e.g., at t3) to similar effect.

This method has been implemented, for example, in Lindner et al (Circulation, 2001) and Rychak et al, (Mol Imaging, 2007).

A key difficulty with this method is that it requires the use of high-power ultrasound to destroy microbubbles, which may introduce unwanted bioeffects. Microbubble destruction caused by high-power ultrasound has been observed to correlate with premature ventricular contractions in the heart (van Der Wouw et al, 2000), alterations in microvascular flow (Hu et al, 2013), and transient poration of nearby cells (Miller et al, 2008). An imaging method that does not require microbubble destruction is therefore preferable from a safety perspective.

Motion-Based and Filter Methods

Various techniques aimed at identifying target-bound microbubbles based on temporal or frequency components have been proposed. These methods may advantageously be used in the mid-phase after microbubble administration, and may be operated in essentially real-time as the ultrasound scan is being performed.

Discrimination of moving from stationary microbubbles by simple visual assessment of a video sequence was described in Willmann et al (2017). It should be apparent that this method may be difficult to implement in the case of a high concentration of circulating microbubbles, in the presence of moderate tissue motion, and requires expertise on the part of the user. A quantitative method that does not rely upon the expertise of the user is preferable for widespread utilization.

Computer-based filtering methods have also been described. For example, U.S. Ser. No. 12/084,933 (Frinking et al) discloses an algorithm whereby the contrast signal can be filtered in the time domain to isolate target-bound from freely circulating microbubbles. A refinement of this method to enable detection of detaching microbubbles is taught in U.S. Ser. No. 12/520,839 (Frinking et al). An interframe averaging method operating on RF data was reported in Hu et al (Am J. Nucl Med Mol Imaging, 2013). U.S. Ser. No. 11/237,221 (Phillips et al) and U.S. Ser. No. 11/805,151 (Guracar) disclose methods for identifying target-bound microbubbles by tracking the relative motion of contrast agents in time.

Methods by which to discriminate circulating from target-bound microbubbles based on the spectral content of their respective echoes have been disclosed in, for example, U.S. Ser. No. 11/237,221 (Phillips et al), U.S. Ser. No. 11/885,723 (Gaud et al), and Dayton et al (2003 IEEE Ultrasonics Symposium).

A key difficulty with the abovementioned methods is that they require spatial co-registration of multiple successive imaging frames, which may be difficult in the presence of tissue motion. Filter-based methods may also be insensitive to low concentrations of target-bound microbubbles in the presence of large concentrations of circulating microbubbles.

Despite the broad potential benefit to medicine, no targeted microbubble products have yet been commercialized for clinical use. Similarly, no analytical software packages for use with targeted microbubbles have been commercialized for clinical use.

The present invention comprises a method, referred to as dynamic scaling ultrasound molecular imaging, for robustly quantifying the magnitude of a contrast signal within a region of interest (ROI) at various points in time. This method is most effectively utilized with a specific composition of microbubble contrast agent. In some embodiments, this method is utilized, with appropriately formulated microbubbles, to image the presence of targeted molecular markers of disease. This invention provides the user with a robust method by which to determine how the contrast signal is changing in time, thereby reducing the uncertainty present in the current state of the art.

In some embodiments, the method of the present invention utilizes the concept of a reference region. As used herein, a reference region refers to a region of the image corresponding to a location within the patient being imaged in which instantaneous contrast signal is representative of the amount of contrast material circulating within the blood pool. The rate at which contrast signal within the reference region changes over time is influenced by a number of factors that may be specific to the particular patient and imaging conditions, such as the microbubble dose, route of administration, disease status (e.g., cardiac status such as heart rate and pumping efficiency), ventilation status (oxygen saturation and use of supplemental oxygen). Such variables can confound interpretation of imaging data. The use of a reference region as discussed in the current application provides a basis for making comparisons across imaging subjects and settings, in addition to its use as a dynamic scaling factor (discussed below).

As used within the context of the present invention, a reference region is further defined as a region in which negligible to no accumulation of microbubbles occurs. The reference region should therefore be carefully selected so as to ensure that this criterion is met. Furthermore, the microbubble should be formulated to as to minimize unwanted accumulation within regions not expressing the imaging target.

Regions of interest comprising a cavity filled with blood and subject to circulatory flow are broadly suitable for use as reference regions. An exemplary reference region is the left ventricular cavity. In some embodiments, the reference regions include the lumens of the aorta, vena cava, femoral artery, carotid artery, renal artery, renal vein, or the like. In other embodiments, the reference regions refer to any well-vascularized tissues exhibiting a spatially uniform microcirculation, such as skeletal muscle remote from lesions and otherwise free from pathology. Poorly vascularized tissues, such as adipose tissue, or tissues exhibiting disorganized vasculature, such as a solid tumor, in some embodiments, are not used as a reference region.

In some embodiments, tissues in which microbubbles (contrast agents) are known to accumulate in the absence of disease, such as the spleen and liver and other sites of high innate immune cell concentration are not suited for use as reference regions in the context of this invention.

The orientation of the reference region with respect to the target tissue is irrelevant in the context of the instant invention. That is, it is not necessary that the reference region be a feeding vessel for the target tissue, although such a reference region may be selected purely for reasons of convenience.

For simplicity it is preferred that the reference region be acquired in the same imaging field of view as the target tissue. Selection of a reference region adjacent to the target tissue offers the ability to address variables related to imaging settings, depth dependent effects; however, use of a reference region adjacent to the target region is not necessary. For example, the use of two or more imaging fields of view from two transducers or one multi-dimensional transducer, one of which images the reference region and the other images a remote target tissue is conceived of Examples of relevant reference regions for specific target tissues are provided in Specific Examples 9-14.

The contrast signal magnitude within the reference region at any instant in time can be represented as a single number, referred to herein as the instantaneous reference intensity, $I_{ref}(t)$. The instantaneous reference contrast signal magnitude may be defined most simply as the average intensity (arithmetic mean) of all the pixels within the reference region; other mathematical representations, such as the median, truncated mean, or root mean squared (quadratic mean), may be used to define the $I_{ref}(t)$ so long as they produce a reproducible representation of the contrast signal magnitude.

As discussed below, use of a reference region in the present invention enables identification of unique time-varying behavior, which facilitates disease diagnosis when using targeted microbubbles.

Dynamic Scaling

The instantaneous contrast signal magnitude within a reference region can be used to scale the contrast signal magnitude within a target region at the same instant. This procedure, referred to herein as dynamic scaling, leads to unexpected behavior that facilitates robust evaluation of ultrasound molecular imaging data.

The dynamic scaling concept taught in the present invention may be applied to ultrasound images or graphically in the form of time-intensity curves.

The details of the method will first be described generally, then in the context of an actual experiment.

FIG. 3A illustrates the general practice of the present invention. A tissue (the target tissue) in a living patient is suspected of harboring disease. It is desired to use ultrasound molecular imaging to determine whether disease is present, and if so to identify the location or locations. It is assumed that the targeted microbubble used in this example is formulated so as to undergo specific adhesion in regions of disease present (that is, the targeting construct is selected so as to bind to a suitable molecular target expressed within the diseased region) and low to essentially no adhesion in regions with absent disease.

For simplicity, the target tissue to be imaged is assumed to contain two sub-regions: one in which the disease is actually absent (Region B), and one in which the disease is actually present (Region C). For the purpose of the current example, it is not necessary that the two sub-regions are contiguous. A third region of interest, Region A, is used as a reference region. It is assumed that Region A meets the criteria for serving as a reference region as discussed above. Note that it is not necessary that the target tissue and reference region are located within the same imaging field of view. However, it is necessary that imaging data obtained from each region be co-registered temporally.

The images in FIG. 3B depict a sequence of simplified contrast ultrasound images from each of the three regions following administration of the targeted microbubble. The magnitude of the contrast signal is shown in levels of grey on a scale of 0.01-4000 (arbitrary units). Before administration of the microbubble (pre-contrast), the contrast signal is uniformly low in all regions. Adjustment of the gain in each region may be performed to produce a similar level of pre-contrast signal within all of the regions of interest, although this is not necessary. The gain is preferably set so that the pre-contrast signal is at the lower end of the dynamic range, whilst not being zero.

Following bolus administration of the microbubble agent the contrast signal magnitude increases rapidly in the reference region. A peak is then achieved, after which the contrast signal is gradually reduced by clearance of microbubbles from the blood pool (mid phase). The contrast signal in the late phase, defined as the point at which circulating microbubbles have been essentially completely eliminated from the reference region, is essentially the same as the pre-contrast signal.

Similar wash-in behavior is found in the early phase for the two targeted regions: a rapid increase in contrast signal that reaches a peak. In the example of FIG. 3B, the magnitude of the contrast signal at peak is higher in the reference region (Region A) than that of the two target tissue regions (Regions B and C), although this is not a necessary requirement for the dynamic scaling method to be used. The contrast signal in the targeted regions then decays in the mid phase; this decay is driven primarily by the clearance of microbubbles from the blood pool. As discussed above, the rate at which the contrast signal decays is dependent upon a number of variables and may vary from patient to patient.

It can be seen that the contrast signal magnitude within the targeted diseased region (Region C) decays more slowly than that within a non-diseased region (Region B) or the reference region (Region A). This is due to the presence of microbubbles accumulated at the sites of target expression within the diseased region. These microbubbles are not removed from the imaged tissue by blood pool clearance mechanisms. The target is not found in the non-diseased region and, with the suitable microbubbles recognized in the art, microbubbles pass freely through this region without accumulation. Microbubbles are not retained within the reference region, as per to the definition of a reference region.

As the imaging study progresses from the wash-in peak to the late phase, the difference in contrast signal magnitude between the diseased and non-diseased regions becomes more prominent. As discussed previously, the contrast signal resulting from the presence of target-bound microbubbles will decay due to destruction of the microbubbles by physical forces (such as deflation caused by gas exchange across the microbubble shell). This decay occurs more slowly than clearance of circulating microbubbles from the blood pool, although the magnitude of the contrast signal magnitude in all regions trends toward the pre-contrast baseline over time (very late phase).

The time-varying behavior depicted in the images can be illustrated in the form of so-called "time-intensity curves" (TIC), in which the contrast intensity or contrast signal magnitude within a given region is plotted as a function of time. In FIG. 4A/B time-intensity curves are shown for the non-diseased region (FIG. 4A) and the diseased region (FIG. 4B); the reference region is overlaid on each time-intensity curve (dotted line). Specific timepoints denoting phases of the contrast agent wash-in and out as illustrated in FIG. 3 are noted on the x-axis: t−1 (Pre-contrast baseline), t0 (administration of contrast) t1 (peak signal), t2 (representative timepoint in mid phase), t4 (representative timepoint in late phase), and t5 (very late). Note that t5 is defined here as the time at which the contrast signal due to target-bound microbubbles is fully eliminated.

Time-intensity curves from each region show similar behavior in the wash-in phase: a rise in contrast signal beginning upon administration of contrast and culminating a peak contrast signal magnitude (M. This is followed by a decay in signal magnitude between t1 and t3. Clearance of microbubbles from the blood pool is completed at t3, and which point the contrast signal within the reference region has returned to baseline. The contrast signal within the non-diseased region similarly reaches pre-contrast baseline at t4 in this example. The contrast signal within the diseased region (FIG. 4B), however, has not reached baseline. Contrast signal in this region subsequently decays at a slower rate (over t3-t5) than during the clearance phase (t1-t3). At a long enough time, the contrast signal within this region also reaches baseline (t5).

The present invention comprises using the instantaneous contrast signal magnitude within a reference region to scale the contrast signal within a targeted region of interest at the same time point. This can be achieved most simply by dividing the contrast signal magnitude within the targeted region of interest by the contrast signal magnitude of the reference region at the same time point. In the example shown in FIG. 3, Region A serves as the reference region, and regions B and C are targeted regions with suspected disease presence.

The corresponding results of the dynamic scaling process as applied to the example of time intensity curves of FIG. 4A-B are depicted and further processed in FIG. 5A-F. The plot for the non-diseased region (Region B, FIG. 5A) decreases over time, owing to the fact that there is no microbubble accumulation within this region and the microbubbles are cleared from this region between t1 and t4.

The reference-scaled contrast signal magnitude in the diseased region of interest (Region C, FIG. 5B) shows an entirely distinct behavior. The scaled signal increases between t1 and t4.

Three salient features of the plots in FIG. 5C and FIG. 5D are noted. First, the difference in polarity of the diseased and non-diseased curves is immediately apparent: the reference-scaled signal increases in the diseased region, and decreases in the non-diseased region. The instantaneous slopes of the reference-scaled contrast signal magnitude are shown in FIGS. 5E, and 5F, and show a (slightly) negative or zero slope for the non-diseased region (FIG. 5E) and a positive slope for the diseased region (FIG. 5F).

Second, the differences in the two regions are detectible between peak signal and full wash-out of the reference region (between t1 and t4). That is, the dynamic scaling method provides information useful for determining differences in contrast signal in diseased and non-diseased regions of interest over a wide time window (not just the late phase).

Third, the average slope of the scaled contrast signal between the peak signal of the reference region (t1) and any arbitrary timepoint between t1 and t4 is positive in the diseased region (e.g., myocardium). The average slope between the same points in a non-diseased region is (in this example) less than zero. The average slope between t1 and various timepoints up to t4 are plotted in FIGS. 5G, and 5H. It can be seen that the average slope for the non-diseased region (FIG. 5G) is negative irrespective of the duration over which the average is computed, so long as said range begins at t1. The opposite is true for the diseased region (FIG. 5H), in which the average slope is everywhere positive.

These characteristics provide for a robust and simple method for establishing whether an observed contrast in any given targeted region of interest is due to target-bound microbubbles as opposed to circulating.

In one embodiment of this method, the reference-scaled contrast signal magnitude is computed within one or more target regions at several timepoints between peak signal and clearance of the reference region. These values are then plotted for each region, and the shape of the curve is evaluated in order to ascertain whether the signal in each region is from target-bound or non-bound microbubbles. In the event that the curve so plotted trends upward over, the presence of target-bound microbubbles is concluded. In the event that the curve trends downward or is predominantly horizontal, it is concluded the absence of target-bound microbubbles. In some embodiments, two, three, four, five or six or more timepoints are evaluated in the methods. In certain embodiments, five timepoints are evaluated in the methods.

In some embodiments, the methods provide that the reference-scaled contrast signal magnitude is computed at peak signal and at a subsequent time point of interest, and the average slope between the two points is computed. In the event that the difference is greater than zero, it is concluded that the observed signal is due to target-bound microbubbles, and hence that the disease in question is present. In the event that the difference obtained is zero or negative, it is concluded that there is no targeted microbubble uptake within the region of interest.

The process at more than one timepoint may be repeated after peak signal is achieved in order to increase confidence in the diagnostic conclusion. For example, the difference may be computed at 1, 3 and 5 minutes after peak signal and the results averaged.

The dynamic scaling method described herein may be performed in a semi- or fully-automated fashion. This process may also be performed either during the ultrasound exam, using software running on the ultrasound scanner, or afterward using software running on a computer workstation.

As should be clear from FIGS. 5G, and 5H, the difference in reference scaled contrast signal magnitude between any arbitrary point and a subsequent point will be positive for diseased tissue and negative (or zero) for non-diseased tissue, provided that the two points are between the peak signal of the reference region and full microbubble clearance from the reference region. As such, this method is especially useful for establishing the presence (or absence) of target-bound microbubbles in the mid-phase.

The dynamic scaling method is also suitable for discriminating between different magnitudes of targeted microbubble accumulation, provided that the imaging timepoints are kept consistent. For example, an average reference scaled slope of 4 would represent a greater degree of targeted microbubble accumulation than a reference-scaled slope of 2 over the same imaging window. The method is therefore useful not just for disease detection (by establishing the presence or absence of targeted microbubbles), but also for evaluating the severity of disease. In some instances, this property is useful in the context of longitudinally following the response of a patient or group of patients to therapy, or for stratifying patients prior to treatment based on severity of disease.

Formation of Reference-Scaled images

The present invention also comprises a method for creating images that enable the user to efficiently determine the presence of target-bound microbubbles. This may be achieved by applying the concept of dynamic scaling to the image. In some embodiments, this is done at the level of single pixels or to groups of pixels.

Formation of reference-scaled images is useful for evaluating the spatial relationship and variability in targeted microbubble accumulation. This may be useful, for example, when the heterogeneity of targeted microbubble signal within a targeted region of interest is believed to convey important information. Additionally, formation of reference-scaled images may be a useful aid to assist with interpretation of quantitative analysis (time-intensity plots and mean slopes).

This concept of reference-scaled contrast images will first be demonstrated on the simplified two dimensional image set of FIG. 3. Each image of the set is re-processed in FIG. 6 such that the new pixel value represents the reference-scaled contrast signal magnitude. Re-scaled images are shown for the two targeted regions, and numbers in parentheses represent the scaled contrast signal magnitude. It can be seen that the scaled signal for the non-diseased region (region B) is low and decreases between peak signal and the late phase. In contrast, the diseased region (region A) increases over the same time period. The difference between the non-diseased and diseased regions is greatest at the late phase, although the differences are apparent at all times between peak signal and the late phase.

The procedure for producing reference-scaled images is described below for a time series of two-dimensional images. Here, pixels are identified by co-ordinates in the x- and y-spatial dimensions and one temporal dimension. Let $I_{a,b}(t)$ represent the contrast signal magnitude of a pixel located at location a,b at time t. Further, let $I_{ref}(t)$ represent the contrast signal magnitude of the reference region at time t. The reference-scaled contrast signal magnitude $I^*_{a,b}(t)$ is computed as $$I^*_{a,b}(t) = I_{a,b}(t)/I_{ref}(t)$$

for each pixel within the imaging field of view. The scaled image is created by replacing $I_{a,b}(t)$ with $I^*_{a,b}(t)$ for each pixel in the image. This process may be performed one or every instant t between peak signal of the reference region and complete loss of contrast signal within the target region.

Figure 6:
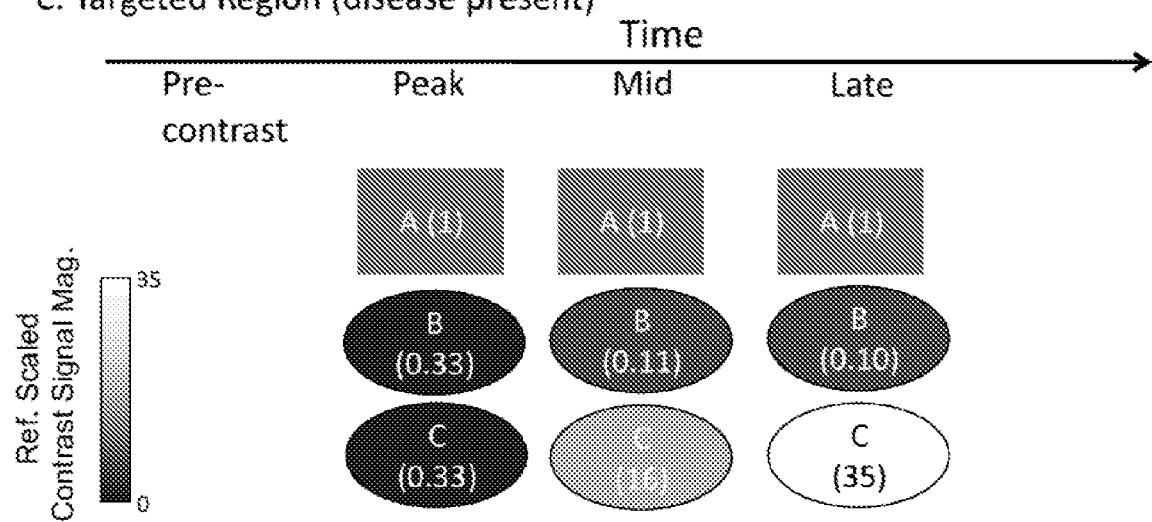
FIG. 6 illustrates the reference-scaled images corresponding to the simplified images of FIG. 3. Numbers in each region represent the reference-scaled contrast signal magnitude at the given time point.

The scaled image is useful for representing the contrast signal magnitude in a reproducible manner independent of patient-specific variables that may confound interpretation. As such, it is useful for making comparisons, for example in assessing the response of a patient before and after a therapeutic treatment. It is also useful for improving the visualization of targeted microbubble accumulation, which may be of low magnitude. In this context, the scaled images may be conveniently presented as a time sequence (as depicted in FIG. 6). Regions of the image in which targeted microbubble accumulation has occurred demonstrate an increasing signal ($I^*_{a,b}(t)$) in time, while the regions in which targeted microbubble accumulation has not occurred demonstrate a decreasing signal.

It is a requirement of the present invention that the scaling procedure be performed using $I_{ref}(t)$ computed from the same time instant as $I_{a,b}(t)$ (e.g., within the same imaging frame).

In practice, it may be convenient to apply the reference scaling only within one or more regions of interest rather than to the entire imaging field of view. For example, the scaling operation may be applied only to the reference region and a region of interest corresponding to a suspect lesion. The scaled image may be conveniently presented as an overlay on the contrast intensity image or brightness (B-mode) image. The overlay may be presented in a color map intended to render salient details conspicuous. For example, the color mapping function may be selected so as to render small differences in different colors, so as to assist in visualizing changes in microbubble retention in the case of low target density.

Additional processing may be applied to the scaled image to diminish the prominence of irrelevant information or to highlight important features in the image. For example, images may be low-pass filtered in the spatial domain. For example, images may be scaled by a constant multiplier (e.g. a gain factor). For example, images may be normalized so as to utilize the full range of pixel display values.

In practice, peak signal (t1) in some embodiments occurs between 1 second and 30 seconds after bolus administration of the microbubble contrast agent. In practice, complete contrast elimination (t5) in some embodiments occurs between 3 minutes and 60 minutes.

In practice, it may be convenient to form the scaled image only at certain timepoints rather than for each frame in a given image data set. For example, representative scaled images may be formed at 10 seconds, 1 minute, and 5 minutes, and the trend in reference-scaled contrast signal magnitude observed in various target regions in order to assess the presence of targeted microbubble retention.

It should be clear that the dynamic scaling procedure may be performed on images of three dimensions using the same procedure. In this case, the unit to be scaled is a voxel defined by spatial three co-ordinates (a,b,c) and a time dimension (t).

Figure 19:
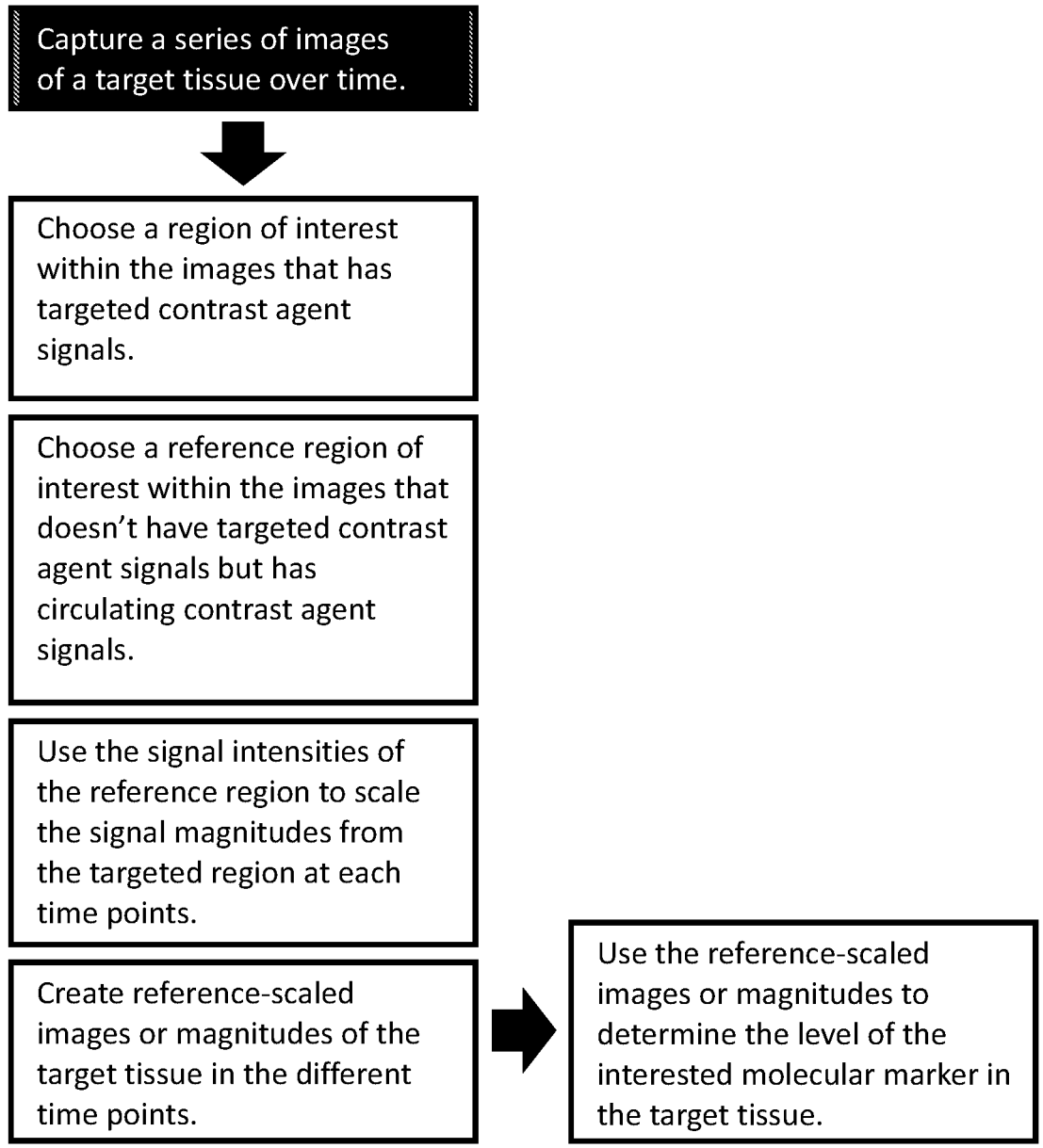
FIG. 19 shows an exemplary flowchart of a dynamic scaling, time-varying manner procedure.

FIG. 19 shows an exemplary flowchart of a dynamic scaling, time-varying manner procedure using the reference-scaled images or magnitudes to determine the level of the interested molecular marker in the target tissue.

In some embodiments, the dynamic scaling, time-varying manner procedure comprises capturing a series of images of a target tissue over time, choosing a region of interest within the images that has targeted contrast agent signals, choosing a reference region of interest within the images that doesn't have targeted contrast agent signals but has circulating contrast agent signals, using the signal intensities of the reference region to scale the signal magnitudes from the targeted region at each time points; creating reference-scaled images or magnitudes of the target tissue in the different time points, and using the reference-scaled images or magnitudes to determine the levels of the interested molecular marker in the target tissue.

In certain embodiments, the dynamic scaling, time-varying manner procedure is performed in units of linearized acoustic power. In certain embodiments, the procedure is performed in units of linearized acoustic amplitude. In certain embodiments, the dynamic scaling, time-varying manner procedure further comprises color coding of the dynamically scaled images or the rate images derived from the rates of change of the dynamically scaled images. In certain embodiments, the dynamic scaling, time-varying manner procedure further comprises smoothing by low-pass filtering of the dynamically scaled images. In certain embodiments, the dynamic scaling, time-varying manner procedure further comprises nonlinear compression of the dynamically scaled images. In certain embodiments, the reference scaled signal magnitude is computed within one or more target regions at several timepoints between peak signal and clearance of the reference region. In certain embodiments, the reference scaled signal magnitude is computed at peak signal and at a subsequent time point of interest, and the average slope between the two points is computed.

Formation of Rate Images

The present invention also comprises a method for formation of a second type of scaled image, referred to herein as a rate image. In this case, the value of each pixel represents the rate at which the scaled contrast signal magnitude changes over a defined period of time.

The rate image conveys information on the rate at which the reference-scaled contrast signal changes, and may be more convenient than a series of scaled images in some applications. For example, when evaluating relative differences between multiple patients, comparison of a single rate image per patient may be preferable to comparing a series of scaled images for each patient. Alternatively, in some applications the rate image may be a more sensitive parameter for conveying desired information than the reference-scaled image.

Figure 7:
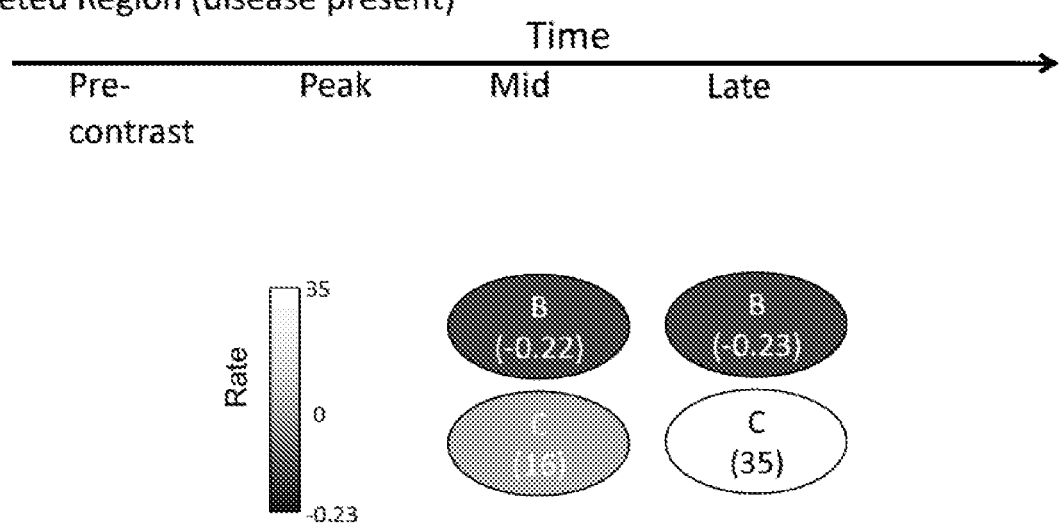
FIG. 7 illustrates the rate images corresponding to the simplified images of FIG. 3. Numbers in each region represent the rate of change of the reference-scaled contrast signal magnitude between peak and the indicated timepoint. The images are in shades of grey to depict positive values and negative values. Rate images for the reference region are uniformly zero by definition, and are omitted here.

FIG. 7 depicts rate images for the imaging data set shown in FIG. 3. Here, images are color-coded in shades of blue and red, representing negative and positive rates, respectively. It can be seen that the non-diseased region (Region B) becomes progressively more blue over time, indicating an increasingly negative rate of reference-scaled contrast signal magnitude. In contrast, the diseased region (Region C) becomes progressively more red over time. The rate scaled images, particularly taken at the late phase, present a simple and convenient way to depict the presence or absence of targeted microbubble accumulation within a given spatial region. The rate $I^{**}_{a,b}(t)$ at time $t=t2$ is computed as:

$$I^{**}_{a,b}(t) = [I^{*}_{a,b}(t2) - I^{*}_{a,b}(t1)]/[t2-t1]$$

$I_{a,b}(t)$ is the scaled contrast signal magnitude of pixel (a,b) at time t; t1 is the time at which peak signal of the reference region is achieved; and t2 is any time between t1 and elimination of contrast from the region of interest.

The rate image is useful for identifying regions of the image in which the scaled contrast signal magnitude increases in time (indicating regions of target-bound microbubble signal). This is especially useful in the case of low target expression, where the contrast signal magnitude due to target-bound microbubbles may be small.

The considerations discussed in the context of the scaled image also apply to the rate image. For example, the rate image may be conveniently displayed as an overlay in which positive, zero, and negative values for the rate are mapped in different color palettes (e.g. reds for positive, black for zero, and blues for negative).

In practice, it may be convenient to form the parametric rate image between any two points between t1 and t3, in which t1 is defined the time of peak signal within the reference region and t3 is the time at which the contrast signal magnitude within the reference region returns to the pre-contrast baseline.

In one embodiment, the rate image is formed using images obtained from any two timepoints between peak signal and full wash-out of the reference region. In a more preferred embodiment, the rate image is formed using images obtained at the peak signal of the reference region and any subsequent point before full wash-out of the reference region.

EXPERIMENTAL

The utility of the dynamic scaling method to improve visualization of targeted microbubble enhancement was assessed in a canine model of transient myocardial ischemia. Temporary ligation of the left anterior descending coronary artery was used to simulate short-duration ischemia, followed by full re-perfusion of the myocardium. This injury induces the rapid expression of CD62 throughout the risk area, suggesting its use as a molecular imaging target for imaging acute post-ischemic injury. It is known that CD62 is expressed at low copy number relative to other cell adhesion molecules (McEver, 2001), and this experiment therefore represents an example of low imaging target density. Additional details of this experiment are provided in Example 7.

Microbubbles targeted to P-selectin were prepared following the method of Example 6. A recombinant human IgG fusion protein that binds to P-selectin was used as the targeting ligand, and functionality for human, mouse, and canine P-selectin was confirmed in vitro.

Animals were anesthetized, then subjected to open-chest ischemia by ligation of the proximal left anterior descending coronary artery. After 10 minutes of ischemia, the ligature was released and the myocardium allowed to re-perfuse. Molecular imaging was performed using the dynamic scaling method after 30 and 90 minutes of re-perfusion. As a negative control, open-chest animals were also imaged prior to induction of ischemia. In some animals, a negative control microbubble formulated with an irrelevant IgG fusion protein as the targeting ligand was administered.

Microbubbles were administered as a bolus by intravenous injection. Imaging was performed at low MI at 1 minute intervals. Short axis images of the left ventricle were acquired, with the same field of view maintained throughout the 5 minute imaging period.

Imaging data was analyzed off line. ROIs encompassing the anterior myocardium (comprising the risk area delineated by perfusion imaging), and the LV chamber (the reference region) were drawn. The average contrast signal magnitude within each ROI was computed in linearized units of acoustic amplitude or power.

After imaging was completed, the LAD suture was re-tightened and a solution of pthalocyanine blue was administered by cardiac puncture in order to delineate the risk area.

Animals were then sacrificed by anesthetic overdose, and the heart excised, washed, and sliced in ~1 cm sections for photographing.

Figure 8:
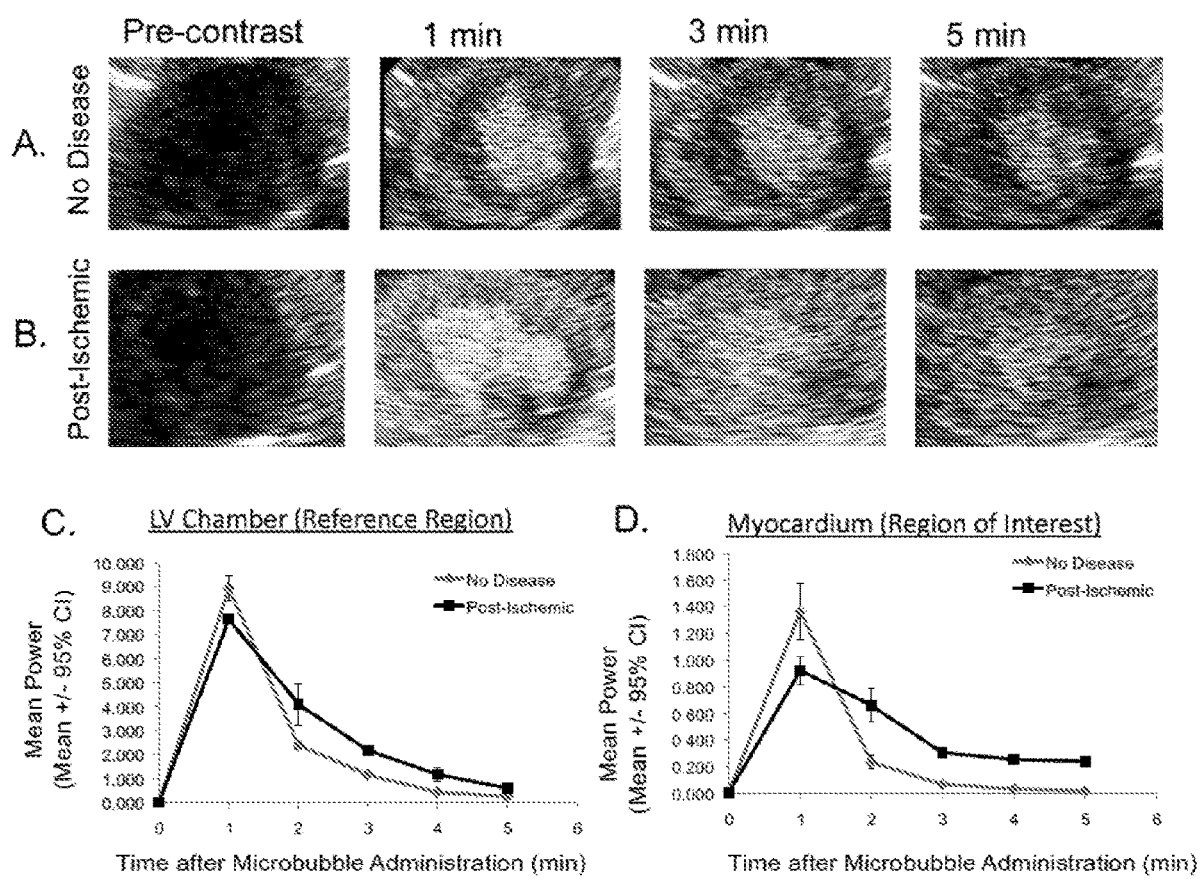
FIG. 8A-D. show exemplary ultrasound molecular imaging of P-selectin in a canine model of myocardial ischemia-reperfusion injury. Representative ultrasound molecular imaging images are shown at various timepoints during the imaging experiment in (8A) a healthy canine not exposed to ischemia, and (8B) the same animal after exposure to 10 minutes of LAD ischemia followed by 90 minutes of re-perfusion. Corresponding time-intensity curves depicting the contrast signal magnitude (expressed in units of acoustic power) in (8C) the LV chamber and (8D) the anterior myocardium.

Similar patterns of contrast enhancement were observed during the early phase after microbubble administration in both post-ischemic and healthy control animals. Contrast enhancement was visible within the LV chamber within 10 seconds of microbubble administration, and subsequently was detected within the myocardium within several heart beats (FIG. 8A, 8B). Slightly greater contrast enhancement within the myocardium was observed in the post-ischemic relative to the healthy control at 3 and 5 minutes. Contrast signal was visible within the LV chamber at 5 minutes (FIG. 8C).

Time-intensity analysis revealed a persistent level of contrast enhancement at 3 and 5 minutes after administration in the post-ischemic animals (FIG. 8D), while contrast signal magnitude returned to near the pre-contrast baseline by 3 minutes in the healthy animal.

The dynamic scaling procedure of the present invention was performed on the time series of images, using the LV chamber as the reference region and myocardium as the target region. As seen in FIG. 9A/B, an increase in reference-scaled signal was observed over the imaging duration (1-5 min following microbubble administration) in the post-ischemic animal. The reference-scaled signal declined slightly over the same time period in the control animal. Similar results were found when the analysis was performed in linearized units of acoustic power (FIG. 9A) and acoustic amplitude (FIG. 9B).

Figure 10:
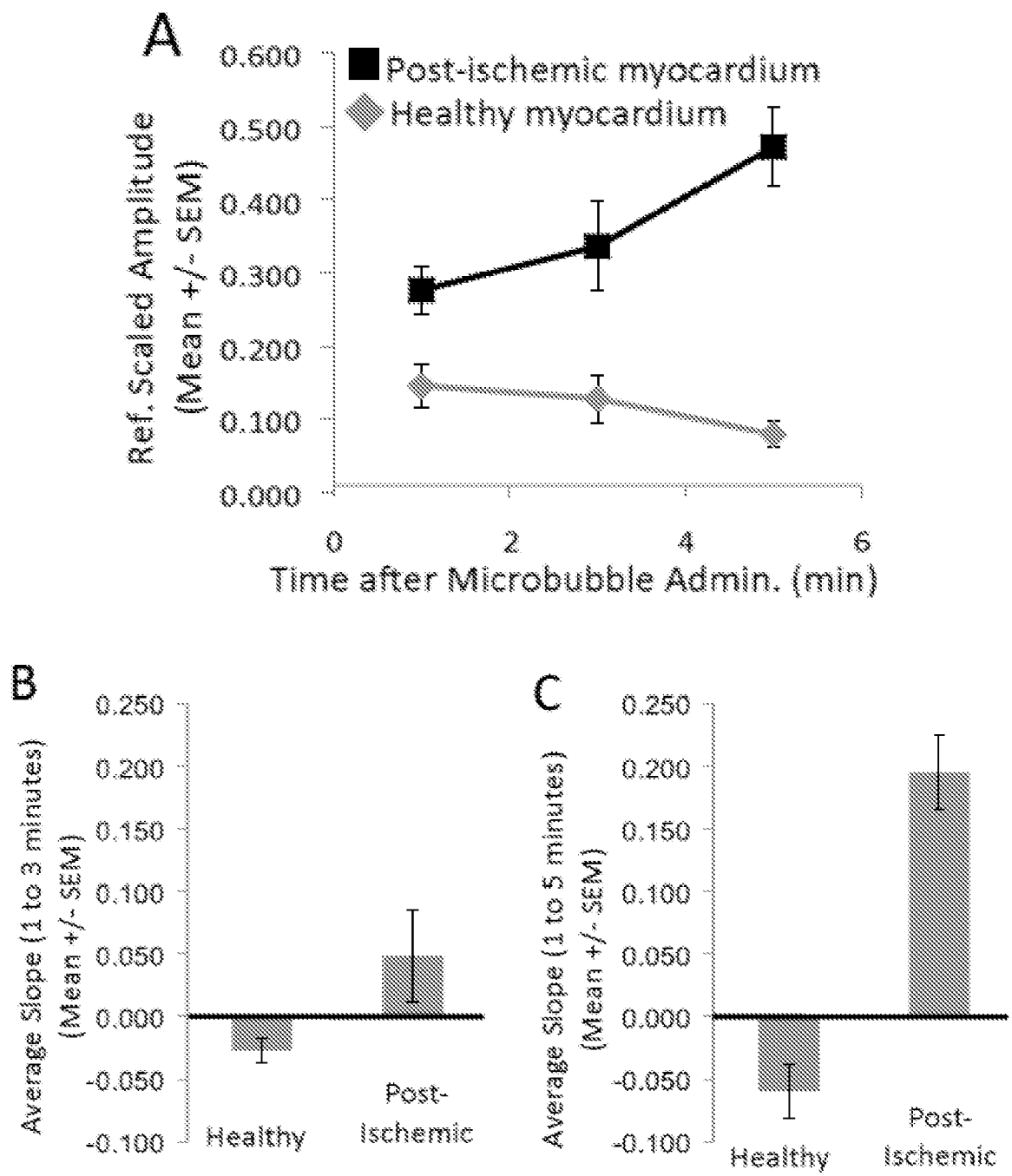
FIG. 10A-C. shows exemplary dynamic scaling ultrasound molecular imaging in canine model of myocardial ischemia-reperfusion. (10A) Reference-scaled contrast signal magnitude at various timepoints after microbubble administration in post-ischemic (squares) and healthy (diamonds) myocardium. The average slope of the reference-scaled contrast signal magnitude between 1 and 3 minutes after microbubble administration (10B), and 1 and 5 minutes after microbubble administration (10C). Error bars represent SEM of n=6 animals.

This experiment was repeated in 5 additional animals. The averaged reference-scaled signal was found to consistently increase between 1 and 5 minutes after contrast agent administration in post-ischemic hearts, and decrease in the healthy heart (FIG. 10A). The average slope of the reference scaled signal was computed between 1 and 3 minutes (FIG. 10B) and 1 and 5 minutes (FIG. 10C). In both cases, the slope was positive for post-ischemic myocardium and negative for non-diseased myocardium.

Linearization

In a preferred embodiment, the dynamic scaling procedure is performed on the linearized contrast signal, rather than the compressed contrast intensity as displayed on a video monitor. Use of the linearized signal, as defined here, maintains the proportionality between the local microbubble concentration and the contrast signal magnitude.

Linearization of the contrast intensity image may be achieved by reversing the compression function and any additional post-processing applied in the formation of the contrast intensity image.

In some embodiments provide a method of detecting a disease in a subject in accordance with the methods for quantifying magnitude of a contrast signal within a region of interest described herein comprising imaging a field of view within the subject for between 1-10 minutes and storing the series of images in a readable computer medium; performing the dynamic scaling, time-varying manner procedure on the obtained image time series; presenting the scaled image sequence or the scaled signal plot such as a time-intensity curve to a user; and determining a disease based on the rates of change of the scaled signals. In some embodiments, the field of view comprises a heart, a kidney, a liver, a breast, a tumor, a prostate, or the like. In some embodiments, the field of view comprises a heart. In certain embodiments, a LV chamber is a reference region and myocardium is a target region. In certain embodiments, a dynamic scaling procedure is performed on the linearized contrast signal.

Figure 11:
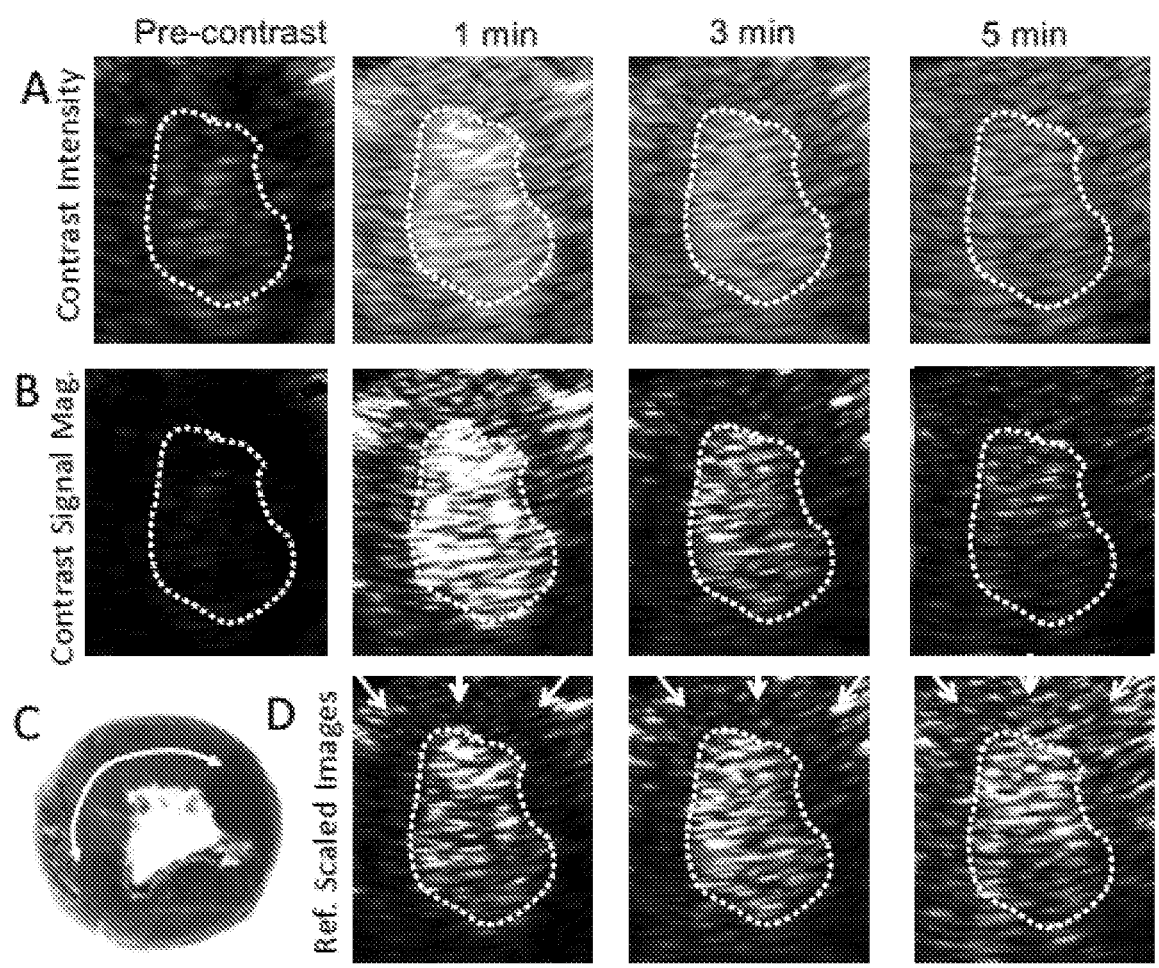
FIG. 11A-D show exemplary dynamic scaling ultrasound molecular imaging in canine model of myocardial ischemia-reperfusion. Images are short-axis end systole acquired at various timepoints before and after P-selectin targeted microbubble administration in a post-ischemic canine. (11A) Contrast intensity images and (11B) corresponding contrast signal magnitude images derived by linearizing the contrast intensity. (11C) Pthalocyanine blue staining of representative short axis section depicting ischemic risk area (arrow). (11D) Reference-scaled images. Arrows highlight region of increasing contrast signal.
Figure 12:
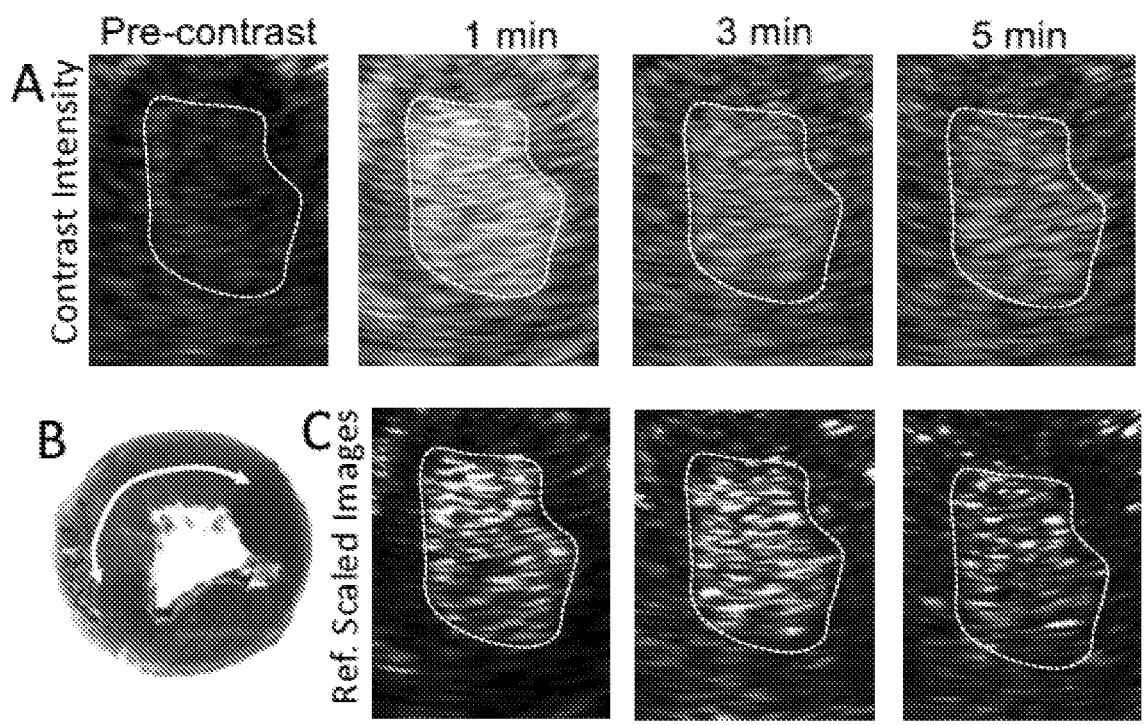
FIG. 12A-C shows exemplary dynamic scaling ultrasound molecular imaging in canine model of myocardial ischemia-reperfusion. Images are short-axis end systole acquired at various timepoints before and after negative control microbubble administration in a post-ischemic canine. A) Contrast intensity images B) Pthalocyanine blue staining of representative short axis section depicting ischemic risk area (arrow). C) Reference-scaled images.

FIGS. 11 and 12 depict an imaging study performed in a living canine 90 minutes after ischemia-reperfusion, as described in before. The region of ischemia was determined by staining ex vivo, and a representative short axis slice depicting the injury location (and expected location of targeted microbubble accumulation) is shown in FIG. 11C. The target in this case is CD62, which is expressed in relatively low copy number under the conditions examined.

The top row (11A) in FIG. 11 depicts a time series of representative end-systolic short axis contrast intensity images before and at three time points subsequent to administration of a CD62-targeted microbubble (the details of the targeted microbubble are provided in Example 6). The pixel values in this image set represent the received echo after compression and post-processing, and are the signal as displayed to the user using existing ultrasound imaging practices. It can be seen that the contrast signal in the myocardium and LV chamber decrease in time, and it is not possible to determine whether the observed signal is due to target-bound or circulating microbubbles.

FIG. 11B depicts the same images after signal linearization. The pixel values in this image represent the contrast signal magnitude as defined in the present invention, and are proportional to the local microbubble concentrations. The large difference in magnitude between the signal in the myocardium and within LV chamber is apparent in this image set. The linearized image does not enable the user to assess the presence of target-bound microbubbles within the myocardium due to the low signal in this region. Therefore, although the linearized image enables direct visualization of the local microbubble concentration, it is not suitable for identifying the presence of target-bound microbubbles in this setting.

FIG. 11D depicts the same images after dynamic scaling of the linearized images. At 1 minute after microbubble administration signal within the LV chamber is appreciated, but low to essentially no signal is noted within the myocardium. At 3 minutes a small signal is appreciated within the anterior myocardium within the disease region, and by 5 minutes a significant signal is observed. This series of images demonstrates an increasing trend in scaled contrast signal, indicating the presence of targeted microbubbles. The dynamically scaled image sequence provides a robust and relatively simple to implement means for identifying the presence of contrast signal due to target-bound microbubbles.

The experiment was repeated in the same animal using a negative control microbubble (e.g., formulated with a targeting ligand that does not enable microbubble retention to CD62). The contrast intensity images shown in FIG. 12A appear similar to those in 11A, in that the signal within the LV and myocardium decreases with time.

FIG. 12C depicts the same image sequence after linearization and dynamic scaling. A signal is appreciated with the LV at all time points. Negligible signal is observed within the myocardium, and no time-dependent increase is observed at any region. The dynamically scaled presentation enables robust determination of the absence of target-bound microbubbles.

7. Imaging Conditions

The present invention uses non-destructive imaging techniques. Non-destructive imaging is charactered to result in a change of 10% or less in the contrast signal due to destruction of microbubbles by the ultrasound beam.

In accordance with practice of the present invention the signal within the reference region is non-zero at all time points. This is achieved most conveniently by setting the gain on the ultrasound scanner at a level such that the noise present in the pre-contrast image is at the low end of the dynamic range. The gain is preferentially set so that the pre-contrast contrast signal magnitude within the reference region is between 0.01 and 5% of the full dynamic range.

In some embodiments, the present invention provides that each image in a time sequence is independent from the preceding images. This is achieved by forgoing temporal filtration, such as persistence. Temporal filtration methods are disclosed, for example, in U.S. Ser. No. 12/084,933 (Frinking et al); such methods are unsuitable for use with the present invention.

In some embodiments, the present invention provides the maintenance of a consistent imaging field of view. This is of high importance for formation of parametric images. At a minimum, two consistent fields of view are required, the first preferably at or soon after peak signal, and the second at or slightly before clearance of the contrast agent from the reference region. In a preferred embodiment, multiple images are acquired at each timepoint, and the best aligned frames are selected.

In some embodiments, the present invention provides that few to essentially no pixels in the contrast image are saturated. In a preferred embodiment less than 5% of pixels within the region of interest or reference region are saturated. In a more preferred embodiment, less than 1% of pixels in said locations are saturated. In a most preferred embodiment, no pixels in said locations are saturated. This is preferentially achieved by utilizing the microbubbles formulated as discussed in the present invention, and following standard practices for setting the ultrasound system gain.

In some embodiments, the present invention provides that the microbubbles undergo low to essentially no accumulation in the absence of the targeted molecule (i.e., low non-specific binding). In a preferred embodiment, fewer than 5% of all adherent microbubbles are retained by non-specific mechanisms. In a more preferred embodiment, fewer than 1% of all adherent microbubbles are non-specifically retained. This is preferentially achieved by utilizing the microbubbles formulated as discussed in the present invention.

The rate at which ultrasound images are acquired (the frame rate) is relevant to the application of the present invention. There is no requirement for a high frame rate (in the range of 10, 30, or higher frames per second) in order to detect the presence of target-bound microbubbles using the present invention; in fact, high frame rates are not preferred due to the possibility of microbubble destruction when using the microbubbles formulated as described in section 8 below. A frame rate of less than 10 frames per second is desirable in the context of the present invention.

In some cases, the frame rate may need to be set so as to facilitate physiological triggering (for example, gating on the ECG when imaging the heart). In some cases, the frame rate may be set to acquire one frame every minute (0.016 Hz). In some cases, it may be convenient to acquire two, three, or five images at 1 minute intervals for the purpose of averaging.

It is preferable that images be acquired using a contrast-specific imaging mode with high sensitivity to microbubble contrast agents and high rejection of the tissue signal. Exemplary imaging modes include contrast pulse sequences (CPS) and power pulse inversion, both of which can be operated at low mechanical index (non-destructive to microbubbles).

8. Contrast Agents (e.g., Microbubble) Formulation Considerations

The dynamic scaling molecular imaging method of the present invention is most advantageously practiced with microbubbles formulated to exhibit certain specific characteristics. The microbubble size distribution is of high relevance, specifically the presence of large microbubbles. Additionally, the pharmacodynamics of the microbubble are important, and non-specific accumulation must be avoided to the greatest extent possible. The microbubble composition may be selected so as to cause the microbubble product to exhibit desirable properties for use in dynamic scaling molecular imaging. A skilled person in the art would readily recognize any suitable contrast agents based on the practice of the present invention for the methods described herein.

For example, the method requires obtaining an accurate representation of the microbubble concentration within a reference region on ultrasound imaging. Moreover, this should be done using non-destructive imaging, preferably at low mechanical index. The ability of the ultrasound to penetrate into the tissue may be limited at reduced mechanical index, preventing visualization of deep tissues. Shadowing of deep structures by microbubbles, whether circulating or target-bound, is undesirable. In some embodiments, this is of particular relevance in the context of cardiac imaging, where a high concentration of circulating microbubbles in the LV chamber can effectively obscure the inferior wall. It is found that this problem may be ameliorated by formulating the microbubble product to have a small diameter. In some embodiments, microbubbles with a mean diameter by number of between 0.1 to 2.0 um 0.2 to 2.0 um 0.3 to 2.0 um 0.4 to 2.0 um 0.5 to 2.0 um 0.6 to 2.0 um or 0.7 to 2.0 um are recommended to use the dynamic scaling method. Additionally, the concentration of large and small microbubbles in the formulation should be low. In a preferred embodiment, the number concentration of microbubbles greater than 10 um in diameter is less than 1%. In a more preferred embodiment, the number concentration of microbubbles greater than 8 um in diameter is less than 1%. In a most preferred embodiment, the number concentration of microbubbles greater than 5 um in diameter is less than 1%.

Figure 13:
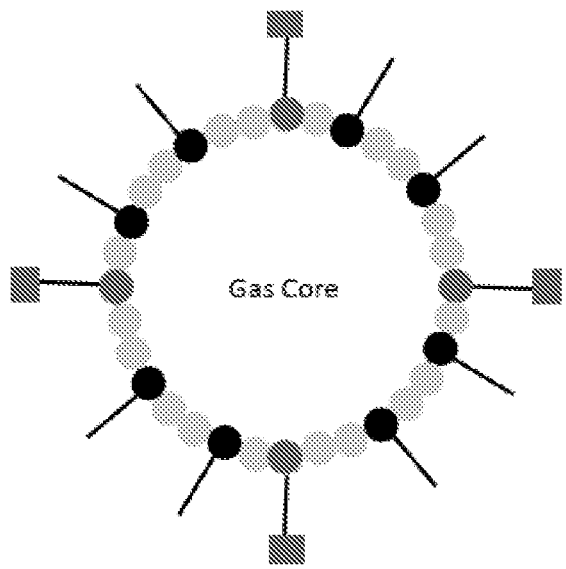
FIG. 13 provides illustrative schematic of a targeted microbubble. Three shell-forming components are described: a shell-forming surfactant, a second surfactant composed of a hydrophobic anchor and a hydrophilic portion, and a targeting construct composed of a targeting ligand, a hydrophilic portion, and a hydrophobic anchor.

Microbubble shells composed of three components are necessary for achieving the size properties required for use in the present invention. The first component is a shell-forming surfactant, which serves to create an encapsulating barrier around the gas core of the microbubble. The second component is a second surfactant, the presence of which serves to modulate the microbubble size. The third component is a targeting construct, which serves to immobilize the targeting ligand to the outer surface of the microbubble shell. Each of the shell components can also modulate the pharmacokinetic behavior of the microbubble. Microbubbles lacking any of these three shell-forming components are not suitable for use in the context of the present invention. FIG. 13 illustrates a representative three shell component microbubble suitable for use in the present invention. In some embodiments, said targeted contrast agent is a microbubble comprising a shell-forming surfactant, a second surfactant, and a targeting construct.

The shell-forming surfactant may be any amphipathic, biocompatible substance that can stabilize the encapsulated gas and offers sufficient flexibility to allow non-destructive oscillation of the microbubble when stimulated by low-MI ultrasound. In practice, some diacyl phospholipids provide these characteristics. In particular, phosphatidylcholines with saturated diacyl tails of between 16 and 20 carbons in length are especially useful.

Shell-forming surfactants consisting of proteins or synthetic polymers tend to provide rigid shells and are therefore not desirable in the context of the present invention. Phospholipids with long acyl chain tails, in particular greater than 20, are similarly not desirable for use in the present invention.

Shell-forming surfactants known to promote non-specific microbubble retention to immune cells, such as phosphatidyleserine, are not preferred within the context of the present invention.

Shell-forming surfactants which do not present a net charge are preferred. Phosphatidylcholines and phosphatidylethanolamines, particularly disteroylphosphatidylcholine, are useful in this regard. Charged phospholipids and fatty acids are not suitable for use as a shell-forming lipid in the context of the present invention. Exemplary materials that are not suitable for use in the present invention include 1,2-dioleoyl-3-trimethylammonium-propane (DOTAP), 2-dipalmitoyl-sn-glycero-3-phosphserine (DPPS), 1,2-distearoyl-sn-glycero-3-phospho-(1'-rac-glycerol) (DSPG), and 1,2-distearoyl-sn-glycero-3-phosphate (DSPA).

The presence of the second surfactant serves to preferentially stabilize small-diameter microbubbles that are desirable in the context of the present invention. Amphipathic substances able to be strongly anchored into the microbubble shell and possessing a hydrophilic polymeric group are suitable as a second surfactant. Headgroup-grafted PEG-lipids exhibit these properties, and are useful in this regard. In particular, diacyl saturated phosphatidylethanolamines (between 16 and 20 carbons in length) bearing a headgroup-grafted PEG of average molecular weight between 500 and 5000 are preferred. Microbubbles formulated without a second surfactant are not desirable in the context of the present invention.

Second surfactants anchored with a single chain fatty acid, such as fatty acid esters of PEG (PEG 40 stearate) are weakly anchored in the microbubble shell, and therefore are not suitable for use in the present invention.

Targeting constructs suitable for use in the present invention comprise a hydrophobic anchor, providing for insertion into the lipid shell; a hydrophilic portion, which serves as a spacer between the ligand and the microbubble shell; and a targeting ligand, providing for binding of the microbubble to the intended molecular target. The targeting construct may be incorporated into the shell upon synthesis of the microbubbles, or may be inserted into the intact microbubble after preparation.

Targeting constructs in which the hydrophilic portion comprises a flexible polymer chain are preferred. In a preferred embodiment, the polymer chain is polyenthyleneglycol (PEG). In one embodiment the average molecular weight of the PEG is between 500-5,000. In a more preferred embodiment, the average molecular weight of the PEG is 2,000.

Examples of hydrophobic moieties suitable for use in the anchor of the targeting construct include branched and unbranched alkyl chains, cyclic compounds, aromatic residues and fused aromatic and non-aromatic cyclic systems. In some instances the hydrophobic moiety will consist of a steroid, such as cholesterol or a related compound. Preferred species include lipids, steroids, and hydrophobic polyamino acids. In a most preferred embodiment, the anchor is a phosphatidyethanolamine with saturated diacyl tails of 16 to 20 carbons in length.

Targeting ligands suitable for use in the present invention are biological or synthetic substances able to mediate firm and specific retention of the microbubble to sites within the imaging subject where the intended molecular target is expressed. Many biomolecules, including antibodies, glycoconjugates, peptides, fusion recombinant proteins, carbohydrates, nucleic acids, and small molecules are broadly suitable for use as targeting ligands within the context of the present invention. In some cases, it may be desirable to synthesize a targeting ligand with a moiety suitable for conjugation to the hydrophilic spacer of the targeting construct. For example, a recombinant protein may be expressed with a terminal cysteine. In some cases, it may be desirable to utilize a chemical crosslinker to conjugate the targeting ligand to the hydrophilic spacer.

Extravisation of microbubbles from the vascular compartment can cause unwanted non-specific retention, and is therefore not desirable in the context of the current invention. The lower limit of the microbubble size distribution should be carefully controlled so as to reduce the possibility of microbubble extravisation. In a preferred embodiment, less than 10% of echogenic microbubbles have a diameter of below 0.7 um.

The composition of the microbubble shell may be varied to achieve microbubble size, pharmacokinetic, and adhesive properties desirable for any particular application. As discussed above, microbubbles with a mean diameter of between 0.7 and 2.0 um and less than 1% by number of particles above 5 um and less than 10% of echogenic particles below 0.7 um are desired in the present invention. Such microbubbles may be formulated by following the considerations below.

The density (by moles) of the targeting construct should be between 0.1 and 5%. The optimal density of anchor molecule is related to the affinity of the targeting ligand for the molecular target. In the case of a low affinity ligand, a targeting construct density at the high end of the range is preferred. In the case of a high affinity ligand, a low density of the targeting construct may be acceptable.

The density (by moles) of the second surfactant should be between 5 and 25%. The optimal density of the second surfactant is related to the size of the hydrophilic portion. In general, use of second surfactants with a large hydrophilic portion (for example, DSPE-mPEG-5000), a density on the low end of the provided range may be suitable to produce microbubbles within the desired size range. In the case of a second surfactant with a small hydrophilic portion (for example, DSPE-mPEG-500), a higher density may be required.

The density (by moles) of the shell forming surfactant should not be less than 75%.

In certain embodiments, the microbubble gas core is composed of a perfluorocarbon that is gaseous at physiological temperatures. In a particularly preferred embodiment, C3F8 is used as the gas core.

In some embodiments provide a method for quantifying magnitude of a contrast signal within a region of interest (ROI) by analyzing a time series of ultrasound molecular images acquired in a dynamic scaling manner, the method comprises administering to a target tissue of a subject a targeted contrast agent such as microbubble to image the presence of targeted molecular markers of disease; selecting a reference region representative of the amount of contrast agent circulating within the blood pool in a dynamic, time-varying manner; imaging said target tissue including the selected reference region; determining the magnitude quantitatively of an area of disease by said dynamic scaling, time-varying manner procedure wherein said targeted contrast agent is configured to be bound to said molecular markers of disease expressed within the diseased region. In certain embodiments, the reference region is defined as a region in which negligible to no accumulation of microbubbles occurs. In some embodiments, said targeted contrast agent is a microbubble with a mean diameter by number of between 0.1 to 2.0 um 0.2 to 2.0 um 0.3 to 2.0 um 0.4 to 2.0 um 0.5 to 2.0 um 0.6 to 2.0 um or 0.7 to 2.0 um. In some embodiments, said targeted contrast agent is a microbubble with a mean diameter by number of between 0.7 to 2.0 um. In some embodiments, said targeted contrast agent is a microbubble. In certain embodiments, said targeted contrast agent is a microbubble selected from the group consisting of a targeted microbubble in Table 2, or the like.

In some embodiments provide a dynamic scaling, time-varying manner procedure comprises a. providing a time series of images depicting a single field of view, b. selecting one or more regions of interest and one or more corresponding reference regions, c. forming a reference-scaled image, and/or a reference-scale signal magnitude in which the region of interest and reference region are obtained at the same instant in the time series, d. performing the scaling operation of (c) on two or more images in the time series to determine the time-intensity relationship of the reference-scaled magnitude quantitatively; wherein the reference-scaled signal increases in the diseased region and decreases in the non-diseased region. In certain embodiments, the separate time-synchronized image sequences are obtained for the reference region and region of interest. In certain embodiments, a dynamic scaling, time-varying manner procedure comprises scaling the value of each pixel within a dynamically scaled image by a constant. In certain embodiments, the dynamic scaling, time-varying manner procedure is performed in units of linearized acoustic power. In certain embodiments, the procedure is performed in units of linearized acoustic amplitude. In certain embodiments, the dynamic scaling, time-varying manner procedure further comprises color coding of the dynamically scaled images or the rate images derived from the rates of change of the dynamically scaled images. In certain embodiments, the dynamic scaling, time-varying manner procedure further comprises smoothing by low-pass filtering of the dynamically scaled images. In certain embodiments, the dynamic scaling, time-varying manner procedure further comprises nonlinear compression of the dynamically scaled images. In certain embodiments, the reference-scaled contrast signal magnitude is computed within one or more target regions at several timepoints between peak signal and clearance of the reference region. In certain embodiments, the reference-scaled contrast signal magnitude is computed at peak signal and at a subsequent time point of interest, and the average slope between the two points is computed.

Definitions

"Microbubble" refers to a gas-encapsulated sphere stabilized by a biocompatible shell and which is suitable for use as an ultrasound contrast agent. Such agents are known by many names in the art, including microballoons, nanobubbles, and microcapsules. The use of the term microbubble refers to any such particle in which the presence of an encapsulated gaseous component is responsible for generating the ultrasound contrast signal.

"Targeting Ligand" or "ligand" refers to any material or substance that may promote targeting of tissues, cells, receptors, and/or marker groups in vitro or in vivo with the compositions of the present invention. The terms "target(s)", "targeted" and "targeting", as used herein, refer to the ability of targeting ligands and compositions containing them to bind with or be directed towards tissues, cells and/or receptors. The targeting ligand may be synthetic, semi-synthetic, or naturally-occurring. Materials or substances which may serve as targeting ligands include, for example, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides.

"Imaging Target" or "Target Receptor" or "Molecular Target" refers to a molecular structure within a cell or on the surface of the cell that is correlated with the presence or absence of disease or other medically significant conditions. In the context of the present invention, imaging targets are accessible to microbubble contrast agents. Exemplary classes of imaging targets include cell-surface receptors for peptide hormones, neurotransmitters, antigens, complement fragments, immunoglobulins and cytoplasmic receptors for steroid hormones, and kinase receptors.

"Animal Model" is defined as a non-human organism that is used in experimental research. Animal models include but are not limited to mice, rats, frogs, zebra fish, non-human primates, equines, canines, cats, swine, and insects.

"Non-destructive Imaging" is defined as ultrasound imaging designed to enable visualization of microbubble contrast agents without causing destruction of said agents. This is generally achieved by using low (less than about 0.30) mechanical index. The distinction between destructive and non-destructive imaging techniques is reviewed in Porter et al (2014). Exemplary non-destructive contrast imaging methods are power pulse inversion and contrast pulse sequences (CPS).

"Region of interest (ROI)": a spatially-defined region within the ultrasound image in which the presence of absence of disease is to be evaluated by the imaging method. Examples are the myocardium, renal cortex, or arterial plaque.

"Target Tissue" is defined as the anatomical region in which the presence of disease is suspected, and for which ultrasound molecular imaging is intended to be used to assess the presence and extent of location. The target tissue may comprise both regions of disease (diseased tissue) and regions of normal tissue.

"Diseased Tissue" or "diseased region" is defined as a biological tissue or organ in which the disease of interest is present, and in which the imaging target is present at a target density greater than that within non-diseased tissue.

"Normal Tissue" or "non-diseased tissue" is defined as a biological tissue or organ in which the disease of interest is not present, and in which the imaging target is absent or present at a target density substantially lower than that in diseased tissue.

"Reference Region" is defined as a spatially defined region in which retention of the microbubble, by specific or non-specific mechanisms, is known to not occur to any significant degree. The reference region is spatially distinct from the target tissue.

"Scaled Image" or "Reference Scaled Image" is defined as an ultrasound image in which the displayed pixel values represent the quotient of the contrast signal magnitude and the contrast signal magnitude of a suitable reference region at the same timepoint. The scaled image may be multiplied by a constant value, or subjected to other processing steps (e.g. low-pass spatial filtering).

"Rate Image" is defined as an ultrasound image in which the displayed pixel values represents the rate at which the scaled contrast signal magnitude changes over a prescribed period of time. The rate image may be multiplied by a constant value, or subjected to other processing steps (e.g. low-pass spatial filtering).

"Target Density" or "target expression level" is defined as the effective concentration of target molecules that are accessible to the administered ultrasound contrast agent.

"Contrast Signal Magnitude" is defined as the magnitude of the echo signal derived from contrast agents within the region of interest. While not wishing to be bound by any particular theory of operation, the contrast signal magnitude may be expressed in terms of the echo power, echo amplitude, RMS squared amplitude, or any other quantity which may be directly proportional to the concentration of contrast agents within the region of interest under the imaging conditions at hand.

"Contrast Intensity" or "video intensity" is defined the magnitude of the echo signal derived from contrast agents within the region of interest after processing for presentation on a video display. Said processing may include dynamic range compression, color mapping, and other post-processing adjustments to make the image diagnostically useful.

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

In certain embodiments, invention aqueous suspensions may include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

All of the various embodiments or options described herein can be combined in any and all variations. The following Examples serve only to illustrate the invention and are not to be construed in any way to limit the invention.

EXAMPLES

Example 1. Preparation of Lipid Emulsion

An emulsion comprising the microbubble shell-forming components was prepared as follows. 50 mL of 0.9% injection grade NaCl (normal saline; Baxter) was placed in a depyrogenated glass vial and heated to 70 deg C. in a water bath. To the saline, 100 mg of disteroylphosphatidylcholine (DSPC), 65 mg of disteroylphosphatidylethanolamine-PEG (2000) (DSPE-mPEG(2000)), and 5 mg of DSPE-PEG (2000)-PDP (all in powder form, and purchased from Avanti Polar Lipids) were added. The lipids were solubilized by low-power sonication for 20 minutes (9 W using a CP-505 sonicator, Cole-Parmer). During the sonication process, the dispersion was observed to transition from opaque to translucent, with no visible solids present.

The emulsions were stored in air-free conditions for up to 6 hours prior to formation of microbubbles.

It will be apparent to one skilled in the art that other emulsification methods will be appropriate in the context of this method.

It will be apparent to one skilled in the art that the method described above can be modified to enable incorporation of a variety of phospholipid and PEG-lipid species, subject to the considerations discussed in Section 8 above.

Example 2. Preparation of Exemplary Microbubbles by Sonication

Microbubbles comprising an octofluoropropane (C3F8) gas core encapsulated by a phospholipid shell were prepared from the emulsion of Example 1. Fifty militers of the emulsion was first heated to 70° C., then microbubbles formed by high-power sonication (30 s at 40 W) while sparging the C3F8 gas (99% pure; Fluoromed). This procedure resulted in the formation of a polydisperse, right-skewed dispersion of lipid-stabilized microbubbles of decafluorobutane, at a concentration of ~4E9 per mL. The resulting microbubble dispersion was then allowed to cool to room temperature. Shell forming materials not incorporated into microbubbles were removed by centrifuging the dispersion for 10 minutes at 1000×G, 15° C. (Allegra 6R bucket centrifuge; Beckman-Coulter) in a 100 mL sealed glass vial with a C3F8 gas headspace and collecting the infranatant with a thin needle. Microbubbles were then re-suspended at a concentration of 2-4E9 per mL in a buffer containing of 300 g/L glycerin, 300 g/L propylene glycol in normal saline, pH 5-6.5 (saline/glycerin/propylene glycol buffer).

Four lots of microbubbles were produced by this method. The size distribution of each lot was assessed by electrozone sensing (Beckman-Coulter Multisizer IV). The number-weighted mean and median are shown in Table 3.

TABLE 3

Size properties of microbubbles prepared as in Example 2.

| Lot | Mean Dia (um) | Median Dia (um) |
|---|---|---|
| 0100 | 1.75 | 1.48 |
| 0200 | 1.99 | 1.63 |
| 0300 | 1.88 | 1.55 |
| 0400 | 1.87 | 1.55 |

Example 3. Preparation of Exemplary Microbubbles by Shaking

Other approaches for preparing microbubbles comprising a method to agitate the emulsion of Example 1 in a C3F8 filled and sealed vial under a temperature around the main phase transition temperature of the lipid mixture by manual shaking or high-speed mechanical agitation. The way of high-speed mechanical agitation is favorable since the size and size distribution of the micro-bubbles can be controlled effectively. A mechanical agitator is used at 4550 rpm in this embodiment, by which the resultant microbubbles can be controlled to have an average diameter of 0.8-2 um by regulating the agitation time of 10-60 seconds.

Example 4. One-Step Preparation of Exemplary Targeted Microbubbles

A targeting construct is first prepared by reacting a thiolated cyclic RGD pentapeptide (Peptides International) with equimolar DSPE-PEG(5000)-maleimide (Avanti) for 6 hours at room temperature under air-free conditions. The peptide-PEG-lipid targeting construct is subsequently purified from reactants by size exclusion chromatography.

A lipid emulsion is prepared by the method of Example 1 from a blend consisting of 2.0 mg/mL DSPC, 1.0 mg/mL DSPE-mPEG(1000), and 1.0 mg/mL of the peptide-PEG-DSPE targeting construct. The dispersion is heated and microbubbles are formed by sonication, as in Example 2.

It will be apparent to one skilled in the art that similar targeting constructs may be prepared using a variety of targeting ligands. For example, a dimeric peptide with specificity to human VEGFR2 may be conjugated to the PEG-lipid anchor, as in Smeege et al (2017), and the lipid-PEG-peptide subsequently combined with the remaining shell-forming components during the emulsification step described in Example 1.

Example 5. Two-Step Preparation of Exemplary Targeted Microbubbles

A humanized monoclonal antibody with specificity for VCAM-1 is concentrated to 5 mg/mL in 0.1 M sodium acetate buffer (pH 5), then reacted with 10 mM sodium periodate for 30 minutes at room temperature. The antibody is then exchanged into fresh acetate buffer and incubated with the heterobifunctional crosslinker PDPH (pyridyldithiol-and-hydrazide) (5 mM) for 1 hour at room temperature. The antibody is then purified by gel filtration (Zeba column) into DPBS with 10 mM EDTA, pH 7.4. This procedure results in derivitization of the antibody with a protected thiol group preferentially bound to the Fc region.

A lipid emulsion is prepared by the method of Example 1 from a blend consisting of 2.0 mg/mL DSPC, 1.0 mg/mL DSPE-mPEG(1000), and 0.2 mg/mL of DSPE-PEG(2000)-PDP. The dispersion is heated and microbubbles are formed by sonication, as in Example 2. The microbubbles are incubated with 1 mM tris (2-carboxyethyl)phosphine-based reducing agent (TCEP; Pierce) to convert the stable PDP residue to the reactive sulfhydryl form. Reducing agent and reduction bi-product is removed by washing the microbubbles three times at 15 deg C. in DPBS/glycerin/propylene glycol buffer. Microbubbles are then concentrated to 2E11 μm²/mL in a final volume of 1.0 mL. 5.0 mg of the PDPH-conjugated antibody is added to the concentrated microbubble dispersion, and allowed to react for 16 hours in a sealed glass vial under a C3F8 headspace with gentle end-to-end rotation at 4 deg C. Unreacted antibody is removed by centrifugation of the microbubbles at 1000×G for 10 minutes. Microbubbles are then re-concentrated to 2E9 per mL and stored in a 3.0 mL glass vial with a headspace of C3F8 gas.

Successful conjugation of the antibody to the microbubble surface is verified by flow cytometry. Five microliters of the microbubble dispersion are incubated with a FITC-conjugated anti-human IgG for 20 minutes at room temperature. Microbubbles are analyzed by flow cytometry for the presence of FITC in comparison to a microbubble incubated with an isotype control.

It will be apparent to one skilled in the art that a wide variety of targeting ligands can be conjugated to the microbubble surface using the method described here. For example, targeting of VEGFR2 may be achieved by conjugation of a single-chain human VEGF protein via thioether bonding, as described in Anderson et al (2010).

Example 6. Preparation of Exemplary P-Selectin Targeted Microbubbles

Microbubbles suitable for imaging P-selectin by dynamic scaling molecular imaging were prepared as follows. An emulsion was prepared by sonication, as in Example 1, from 2.0 mg/mL of 18:0 DSPC (Avanti Polar Lipids, #850365), 1.3 mg/mL DSPE-mPEG(2000) (Avanti, #880120) and 0.5 mg/mL DSPE-PEG(2000)-PDP (Avanti #880127). The dispersion was heated and sonicated in the presence of C3F8 gas to create microbubbles and subsequently washed, as in Example 2. This procedure results in the formation of a polydisperse dispersion of lipid-stabilized microbubbles of C3F8, at a concentration of 2-4E9 per mL. The microbubbles were then incubated in 4.0 mM tris (2-carboxyethyl) phosphine (Thermo #777720) for 30 minutes at room temperature to convert PDP into the reactive sulfhydryl, then washed three times to remove the reducing agent. The microbubbles were then incubated with 5 molar equivalents of a selectin-binding targeting ligand for 4 hours at room temperature, followed by 12 hours at 4 deg C. The targeting ligand used here is a recombinant protein consisting of the human IgG1 Fc domain fused to the extracellular portion of an endogenous human P-selectin binding glycoprotein. The targeting ligand was prepared with a reactive maleimide group (SMCC; Thermo #22360) to enable conjugation to the microbubble surface via a thioether bond. After conjugation, the microbubbles were washed three times to remove free ligand, and stored for up to 3 months at 4 deg C. under a headspace of C3F8 gas. Three such lots were prepared and analyzed as discussed below.

Figure 14:
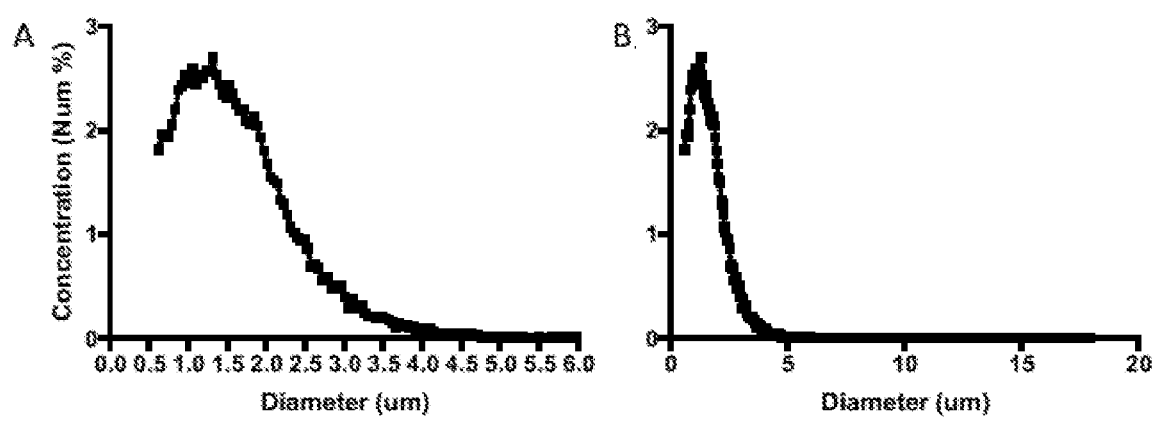
FIG. 14A-C illustrate exemplary P-selectin targeted microbubbles prepared as in Example 6. Representative size distributions obtained by electrozone sensing shown over 14A low end and 14B full range. 14C shows size information obtained for three representative lots of the P-selectin targeted microbubbles.

The shell composition was assessed by reverse-phase HPLC. The shell-forming surfactant (DSPC) composed 87.7% (by moles), the second surfactant (DSPE-mPEG (2000) composed 8.2%, and the targeting construct (DSPE-PEG(2000)-ligand) composed 4.0%. The size distribution was assessed by electrozone sensing. By number, the microbubbles exhibited a mean and median diameter of 1.4 and 1.2 um, respectively. 0.3% of all microbubbles were of diameter larger than 5 um, and 7.3% of microbubbles were of diameter smaller than 0.7 um. Representative size distributions are shown in FIG. 14.

Specific adhesion of the microbubbles to canine P-selectin was assessed by static adhesion assay. Primary canine endothelial cells (CnAEC; Cell Applications) were grown to near confluency in 96 or 24 well plates. On the day of the experiment, the cells were stimulated to express P-selectin by incubating with LPS (100 ng/mL final concentration) for 3 hours. The microbubbles were diluted to a concentration of $1 \times 10^7$ microbubbles per mL, and a 40 uL aliquot was added to each well. The plate was inverted for 5 minutes to enable the microbubbles to contact the cells, then rinsed three times with 100 uL of culture media. The number of microbubbles remaining bound to the cell monolayer was determined by transillumination microscopy (Zeiss Axioskop, x200) in 10 fields of view for each well, and n=4 wells were measured for each condition. As a negative control, wells were pretreated with 20 ug/mL of recombinant human PSGL-1 to block selectin-mediated binding. Approximately 10 times more microbubbles (>30 per field of view) were observed bound on LPS-stimulated monolayers than on unstimulated cells or stimulated cells pretreated with the P-selectin blocker (2-3 microbubbles per field of view).

It will be clear from the above description that the microbubbles so prepared meet the criteria for use in dynamic reference scaling molecular imaging.

The microbubbles prepared in this example were used to image acute reperfusion injury in canine myocardium, as discussed in Example 7.

Example 7: Imaging P-Selectin in Canine Myocardium

The utility of the dynamic scaling method to improve visualization of targeted microbubble enhancement was assessed in a canine model of transient myocardial ischemia. Temporary ligation of the left anterior descending coronary artery was used to simulate short-duration ischemia. This injury induces the rapid expression of CD62 throughout the risk area, suggesting its use as a molecular imaging target. It is known that CD62 is expressed at low copy number relative to other cell adhesion molecules (McEver, 2001), and this experiment therefore represents an example of low imaging target density.

Microbubbles targeted to P-selectin were prepared as in Example 6. Three lots of microbubbles were prepared and used in the in vivo imaging experiments of this example.

Six adult male beagles were used in for the in vivo imaging experiment. Animals were anesthetized, then subjected to open-chest ischemia by ligation of the proximal left anterior descending coronary artery. The region of ischemia was assessed by myocardial perfusion imaging using a non-targeted microbubble (Targestar-P; Targeson). After 10 minutes of ischemia, the ligature was released and the myocardium allowed to re-perfuse. Molecular imaging with the microbubble formulated to target P-selectin was performed at 30 and 90 minutes of re-perfusion. As a negative control, open-chest animals were also imaged prior to induction of ischemia. In some animals, a negative control microbubble formulated with an irrelevant IgG fusion protein as the targeting ligand was administered.

Ultrasound imaging was performed on a Sequoia c512 (Siemens Medical Solutions) with a 4V1c probe operating at a center frequency of 2.0 MHz. Dynamic range was set at 60 dB, post-processing settings S1/0/0/7, and mechanical index between 0.17 to 0.23. Contrast imaging was performed using a Cadence CPS.

Microbubbles were administered as a bolus of 4E7 microbubbles per kg (~300 uL of per dose), followed by a 10 mL saline flush. Imaging was performed at low MI at 1 minute intervals over a 5 minute duration. Short axis images were acquired, with the same field of view maintained throughout the 5 minute imaging period.

Imaging data was analyzed off line. ROIs encompassing the anterior myocardium (comprising the risk area delineated by perfusion imaging), the lateral wall (remote from the risk area) and the LV chamber were drawn. The average contrast signal magnitude within each ROI was computed in linearized units of acoustic amplitude or power. Four end-systolic frames were averaged for each data point.

After imaging was completed, the LAD suture was re-tightened and a solution of pthalocyanine blue was administered by cardiac puncture in order to delineate the risk area. Animals were then sacrificed by anesthetic overdose, and the heart excised, washed, and sliced in ~1 cm sections for photographing.

Similar patterns of contrast enhancement were observed during the early phase after microbubble administration in both post-ischemic and healthy control animals. Contrast enhancement was visible within the LV chamber within 10 seconds of microbubble administration, and subsequently was detected within the myocardium within several heart beats (FIG. 8A/B). Slightly greater contrast enhancement within the myocardium was observed in the post-ischemic relative to the healthy control at 3 and 5 minutes. Contrast signal was visible within the LV chamber at 5 minutes (FIG. 8C).

Time-intensity analysis revealed a persistent level of contrast enhancement at 3 and 5 minutes after administration in the post-ischemic animals (FIG. 8D), while contrast signal magnitude returned to near the pre-contrast baseline by 3 minutes in the healthy animal.

Figure 9:
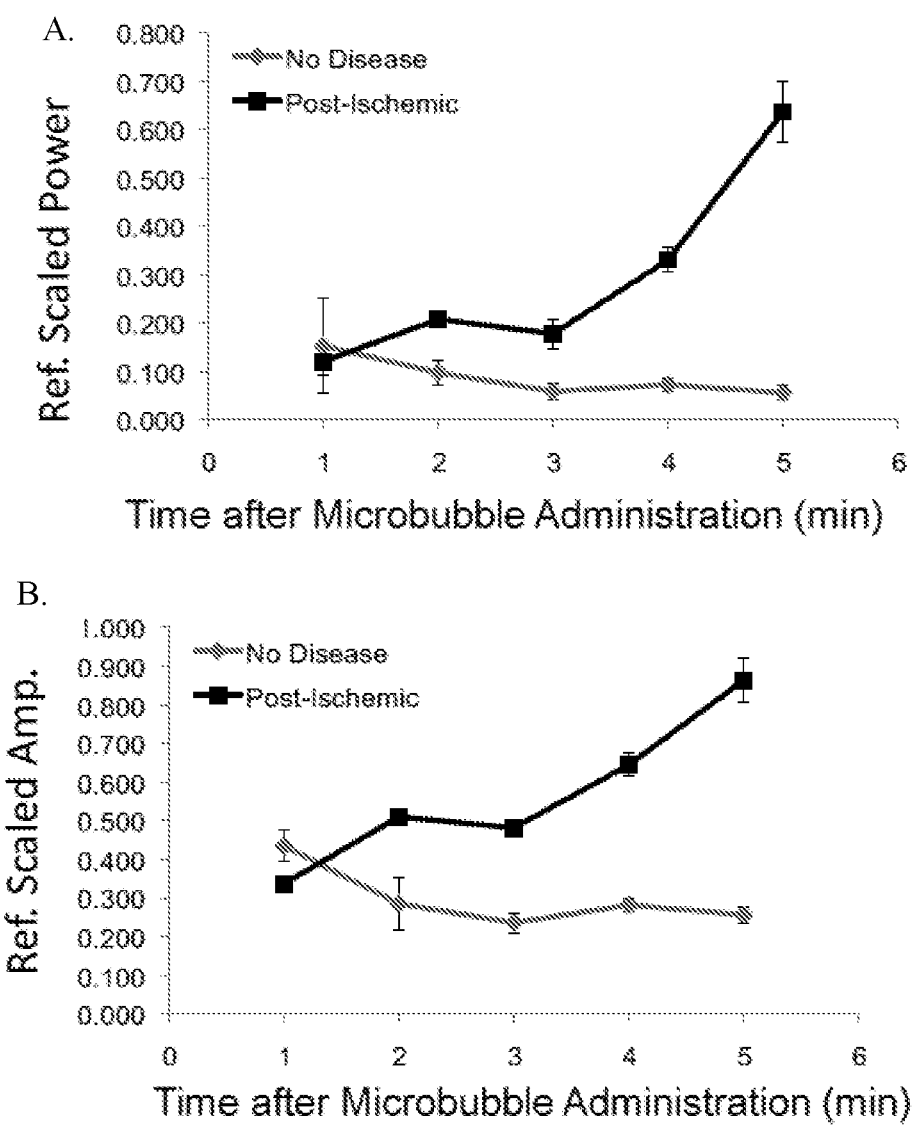
FIG. 9A/B shows the reference-scaled contrast signal magnitude derived from the images of FIG. 8, expressed in units of (9A) acoustic power and (9B) acoustic amplitude.

The dynamic scaling procedure of the present invention was performed on the time series of images, using the LV chamber as the reference region and myocardium as the target region (FIG. 9). An increase in reference-scaled signal was observed over the imaging duration (1-5 min following microbubble administration) in the post-ischemic animal. The reference-scaled signal declined slightly over the same time period in the control animal. Similar results were found when the analysis was performed in linearized units of acoustic power (FIG. 9A) and acoustic amplitude (FIG. 9B).

This experiment was repeated in n=5 animals. The averaged reference-scaled signal was found to consistently increase between 1 and 5 minutes after contrast agent administration in post-ischemic hearts, and decrease in the healthy heart (FIG. 10A). The average slope of the reference scaled signal was computed between 1 and 3 minutes (FIG. 10B) and 1 and 5 minutes (FIG. 10C). In both cases, the slope was positive for post-ischemic myocardium and negative for non-diseased myocardium.

Example 8: Preparation of Exemplary Microbubbles

Microbubbles consisting of an octofluoropropane gas core encapsulated by a phospholipid shell were prepared as follows. An emulsion was prepared following the method of Example 1 from 100 mg of the lipid DSPC (Avanti), 50 mg of PEG-40 stearate (Sigma), and 1 mg of (DSPE-PEG(2k)-PDP; Avanti). Microbubbles were then prepared by sonication in the presence of C3F8 gas. The shell composition, as assessed by HPLC, was 75% DSPC (first surfactant), 24% PEG40s (second surfactant), and 1% DSPE-PEG(2000)-PDP (targeting construct). The microbubbles were then conjugated to a recombinant protein that recognized P-selectin, as in Example 5. This formulation resulted in the formation of a polydisperse, right-skewed dispersion as assessed by electrozone sensing. The number-weighted mean and median diameter were 2.7 and 2.6 um, respectively. 2.7% of microbubbles were of above 5 um in diameter.

In a second experiment, microbubbles consisting of an octofluoropropane gas core encapsulated by a phospholipid shell were prepared using the composition of Example 6. The microbubbles were then allowed to settle in a vial containing PBS for 3 minutes, and the bottom 50% of the dispersion was removed and discarded. The vial volume was replenished with fresh PBS, and the procedure repeated three more times. This procedure removed a substantial portion of the small-diameter microbubbles, leaving a formulation enriched in large microbubbles. The mean and median diameter of the enriched dispersion was 2.3 and 2.1 um, respectively. 2.16% of the microbubbles were above 5 um in diameter.

Figure 15:
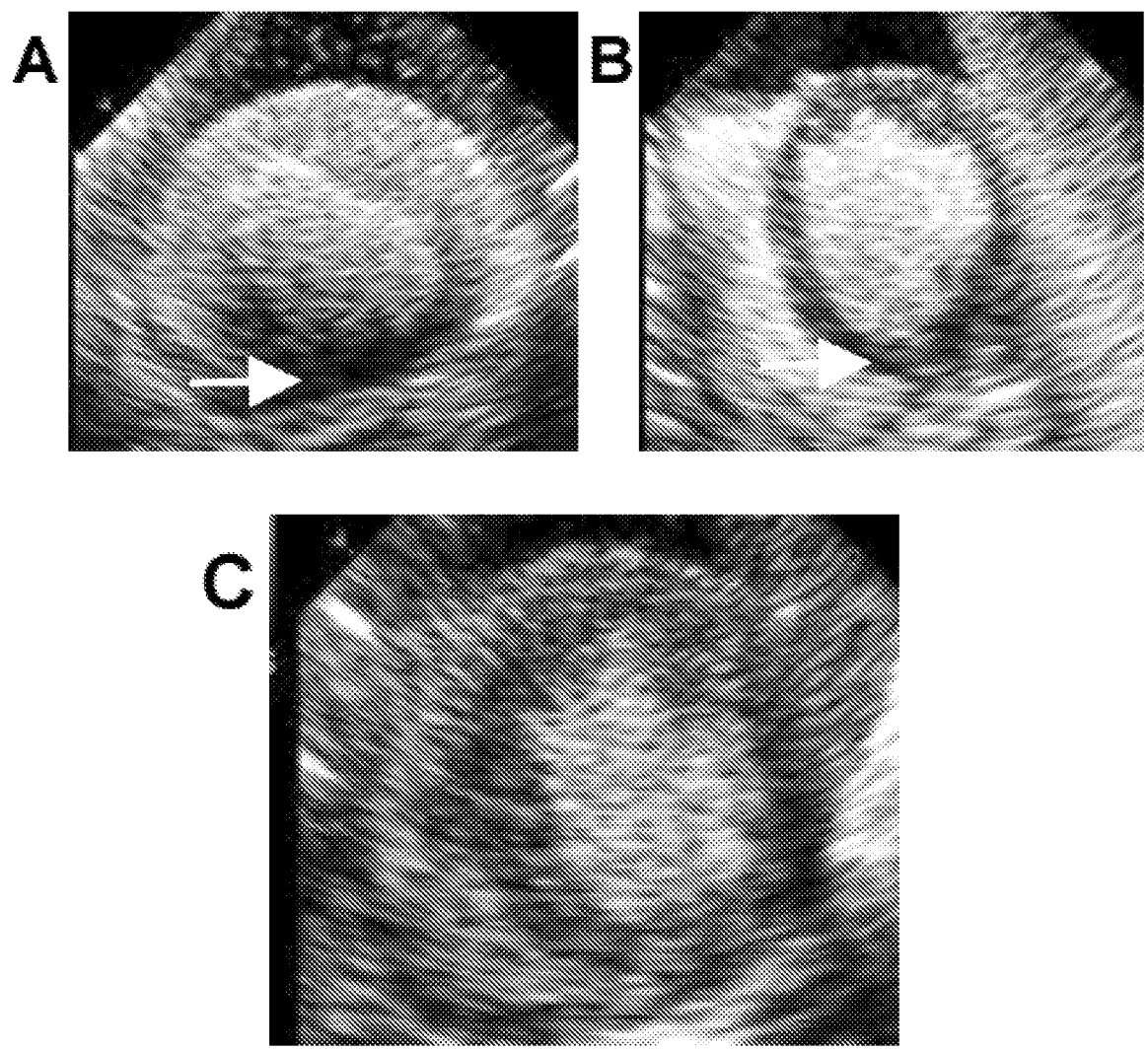
FIG. 15A-C shows exemplary ultrasound molecular imaging of P-selectin in a canine model of myocardial ischemia-reperfusion injury. Representative ultrasound molecular imaging images obtained in a 90 minute post-ischemic canine heart. Images were obtained approximately 1 minute after administration of (15A) P-selectin targeted microbubbles prepared using the formulation of Example 8, (15B) P-selectin microbubbles prepared as in Example 6 and subsequently up-sized as described in Example 8, and (15C) P-selectin targeted microbubbles of the optimal diameter prepared as in Example 6. Arrows depict regions of contrast signal loss.

The two microbubble formulations prepared in this example were used to image acute reperfusion injury in the canine myocardium, as described in Example 7. It was found that both formulations resulted in significant shadowing of the posterior myocardium over at least the first minute following administration (FIG. 15A-C). Additionally, the interior of the LV chamber was inhomogeneous due to shadowing. This prevented the dynamic scaling method from being used, as the target region (posterior myocardium) could not be visualized and the reference region (LV chamber) exhibited signal drop out due to shadowing. In contrast, microbubbles formulated as in Example 6 were found to be suitable for dynamic scaling molecular imaging (Example 7).

Example 9: Imaging Acute Ischemia-Reperfusion Injury in Human Myocardium

The dynamic scaling molecular imaging method of this invention is useful for the detection of acute ischemia-reperfusion injury, as commonly occurs in patients suffering from coronary artery disease. In this case, P-selectin (CD62), which is up-regulated on microvascular endothelium in this condition (Jones et al, 2000; Thomas et al, 2010), may be used as a molecular imaging target. The microbubble is formulated with a targeting ligand that binds specifically to CD62. Suitable microbubbles are disclosed in Specific Example 6.

Figure 16:
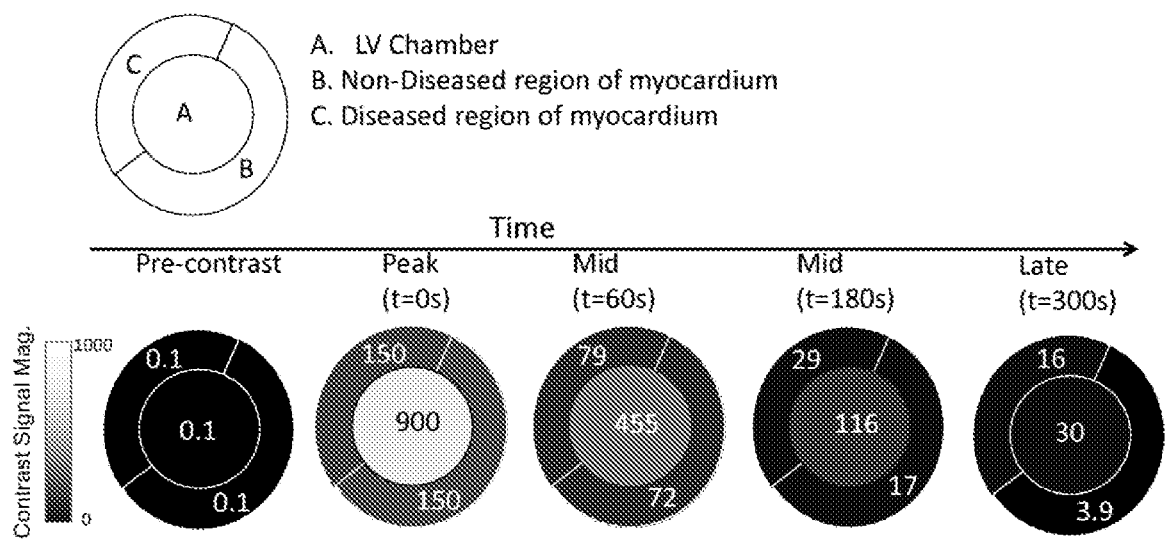
FIG. 16 provides a certain embodiment of an example of ultrasound molecular imaging of ischemic injury in human myocardium. The target tissue in this example is the myocardium, and is assumed to contain two regions: Region B (in which the myocardium has not been exposed to prior ischemia) and Region C (which underwent prior ischemia). The LV chamber (A) serves as a reference region. The bottom panel depicts representative images acquired at various timepoints during the imaging session. The pixel intensity (here depicted in shades of grey) corresponds to the contrast signal magnitude. The numbers in each region represent the contrast signal magnitude at the given timepoint.

A simplified short-axis schematic of the left heart is utilized for simplicity in this example. As shown in FIG. 16, the heart is divided into three regions: A) the left ventricular cavity, B) a region of myocardium remote from the ischemia and in which CD62 is not up-regulated, and C) a region of myocardium exposed to transient ischemia and in which CD62 is up-regulated.

The bottom panel of FIG. 16 depicts a sequence of contrast ultrasound images following administration of the P-selectin targeted microbubble formulation. The numbers in each region represent the contrast signal magnitude, represented in levels of grey. Before administration of the microbubble (pre-contrast), the contrast signal is uniformly low in all regions. Following administration of the microbubble the contrast signal increases in all regions of the image and achieves a peak; the peak signal within the LV chamber is significantly higher than that in the surrounding myocardium, owing to the greater density of blood (and hence contrast material) in this region. The contrast signal then decays as microbubbles are cleared from the blood pool.

The contrast signal magnitude within the targeted diseased region of myocardium decays more slowly than that within a non-diseased region or the LV chamber. This is due to the presence of microbubbles accumulated at the sites of P-selectin expression within the diseased region. The target is not found in the non-diseased region and, assuming that the microbubbles have been formulated following the considerations discussed in section 7, microbubbles pass freely through this region without accumulation. Similarly, microbubbles are not retained within the LV chamber. It should be clear that the interior of the LV chamber can serve as a reference region as used in the context of the present invention for this imaging study.

FIG. 17A-E depict the time-intensity curves derived for this example. The contrast signal magnitude is plotted in FIG. 17A (linear scale), and minimal difference between the post-ischemic and non-ischemic regions of myocardium are apparent. The reference-scaled signal is plotted in FIG. 17B, and the difference between the two myocardium regions is easily visible. The mean slope of the reference-scaled signal between t=60 s and t=90 s, t=180 s, and t=300 s is plotted in FIG. 17C. It can be appreciated that the mean slope within the post-ischemic region increases in time, while that of the non-ischemic region remains zero or slightly negative.

Reference-scaled images are depicted in FIG. 17D. The numbers in each of the three regions represent the reference-scaled contrast signal magnitude. The color of each region has been re-coded to now represent the scaled contrast signal magnitude. It can be seen that the scaled contrast signal magnitude increases in time within the post-ischemic region, and remains constant or slightly declines in the other regions.

FIG. 17E depicts rate images. Here, the numbers in each region represent the rate at which the reference-scaled contrast signal magnitude has changed between peak intensity and the current timepoint. It can be seen that the rate is positive at all time points within the region in which targeted microbubble accumulation occurs (upper left), and is negative in the other regions. Additionally, the difference between the diseased region and non-diseased region increases with time.

Example 10: Detection of Post-Ischemic Renal Injury in Man

The method of this invention is useful for the detection of ischemia-reperfusion injury in the kidney, as may occur in the context of renal transplantation. In this case, the endothelial adhesion molecule VCAM-1 can serve as a molecular marker of disease (Hoyt et al, 2015). The post-ischemic injury is not focal but involves the entirety of the kidney, and up-regulation of VCAM-1 is expected throughout the renal cortex. The renal cortex therefore serves as the target region in this example, and the venal vein can be used as a reference region.

VCAM-1 targeted microbubbles (Prepared using the methods described in Specific Examples 4 and 5) are administered intravenously to a patient suspected of suffering from post-ischemic renal injury. The kidney is imaged using non-destructive ultrasound contrast imaging over 0-15 minutes following microbubble administration. A single field of view, encompassing a representative section of renal parenchyma and the main renal vein, is acquired and maintained throughout the full imaging duration.

Contrast-mode images are selected at 1 minute intervals over the imaging period. The images are linearized, and the mean contrast signal magnitude within the lumen of the venal vein is computed for each image. The pixels within the renal parenchyma (including the renal cortex) are scaled by the reference contrast signal magnitude in each image to form a time series of reference-scaled contrast signal magnitude images.

The image series is reviewed, and the trend in scaled signal within the target region is assessed. An increasing trend within the target region constitutes a positive finding for post-ischemic injury, while a negative or zero trend constitutes a negative finding.

Example 11: Detection of Unstable Atherosclerotic Plaque in Man

The method of this invention is useful for the detection of intra-plaque inflammation, as may occur in the context of unstable atherosclerotic disease. In this case, the cell adhesion molecule JAM-A can serve as a molecular marker of disease (Zhang et al, 2016). In this example, the body of an atherosclerotic plaque found within a carotid artery is the target region, and lumen of the carotid artery distal to the plaque can serve as the reference region.

JAM-A targeted microbubbles (Prepared using a humanized JAM-A binding antibody by the methods of Specific Examples 4 and 5) are administered intravenously to a patient suspected of suffering from unstable atherosclerosis. A segment of the carotid artery is imaged using non-destructive contrast ultrasound imaging over 0-15 minutes following microbubble administration. A single field of view, containing the plaque and also a portion of plaque-free vessel, is acquired and maintained throughout the full imaging duration.

End-systolic contrast-mode images are selected at 3 minute intervals over the imaging period. The images are linearized, and the mean contrast signal magnitude within the reference region and the target region is computed for each image. The mean contrast signal magnitude is determined for three end systolic images at each timepoint, and the results averaged For each timepoint, the mean contrast signal magnitude of the target region is divided by that of the reference region, and the quotient plotted as a function of time.

The reference-scaled time-intensity curve series is reviewed, and the trend in scaled signal within the target region is assessed. An increasing trend within the target region constitutes a positive finding for post-ischemic injury, while a negative or zero trend constitutes a negative finding.

Example 12: Identification of Ovarian Breast Lesions

The method of this invention is useful for the evaluation of ovarian lesions suspected of malignancy. In this case, the pro-angiogenesis receptor tyrosine kinase VEGFR2 can serve as a molecular marker of disease (Willmann et al, 2017). In this example, the location of the lesion within the ovary is identified by B-mode ultrasound, and serves as the targeted region. A volume of skeletal muscle in the thigh serves as a reference region.

VEGFR2-targeted microbubbles (Prepared using the methods described in Specific Examples 4 and 5) are administered intravenously to a patient suspected of ovarian malignancy. A region of ovary containing the lesion is imaged using non-destructive contrast ultrasound imaging over 0-10 minutes following microbubble administration. Additionally, a section of skeletal muscle on the thigh is similarly imaged using a second ultrasound transducer over the same time period.

One end-systolic contrast-mode image each from the ovary and muscle selected at 1 minute and 10 minutes following microbubble administration. The images are linearized, and the mean contrast signal magnitude within the reference region and the target region is computed for each image. The mean contrast signal magnitude of the target region is divided by that of the reference region at each of the two timepoints, and the mean slope is computed.

The mean slope of the reference-scaled contrast signal magnitude is reviewed, and used to assess the presence of targeted microbubble uptake within the ovary lesion. A positive slope is considered to be evidence of positive microbubble accumulation, and hence a likelihood that the lesion is malignant. A zero or negative slope would be evidence of no microbubble accumulation.

Example 13: Identification of Malignant Breast Lesions in Man

The method of this invention is useful for the evaluation of breast lesions suspected of malignancy. In this case, the pro-angiogenesis receptor tyrosine kinase VEGFR2 can serve as a molecular marker of disease (Willmann et al, 2017). In this example, the lesion within the breast is identified by B-mode ultrasound, and serves as the targeted region. The interior of the left ventricle serves as a reference region.

VEGFR2-targeted microbubbles (Prepared using the methods described in Specific Examples 4 and 5) are administered intravenously to a patient suspected of breast malignancy. A region of breast containing the lesion is imaged using non-destructive contrast ultrasound imaging over 0-18 minutes following microbubble administration. Additionally, the LV chamber is similarly imaged using a second ultrasound transducer over the same time period.

One end-systolic contrast-mode image each from the breast and LV chamber selected at 1 minute and 10 minutes following microbubble administration. The images are linearized, and the mean contrast signal magnitude within the reference region and the target region is computed for each image. The mean contrast signal magnitude of the target region is divided by that of the reference region at each of the two timepoints, and the mean slope is computed.

The mean slope of the reference-scaled contrast signal magnitude is reviewed, and used to assess the presence of targeted microbubble uptake within the breast lesion. A positive slope is considered to be evidence of positive microbubble accumulation, and hence a likelihood that the lesion is malignant. A zero or negative slope would be evidence of no microbubble accumulation.

In the event that the slope computed as described herein is judged to be non-diagnostic (for example, it is only slightly positive relative to the slope magnitude observed in other patients with malignancy), the process is repeated using a later timepoint. In this case, the mean reference-scaled slope is computed using images acquired at 1 and 15 minutes.

Example 14: Evaluation of Response to Angiogenic Therapy in Man

The method of this invention is useful for assessing the response of a patient to pro-angiogenic therapy, for example in the treatment of peripheral vascular disease. In this case, the integrin alphav-beta5 can serve as a molecular marker of positive angiogenic response (Leong-Poi et al, 2005). The desired angiogenic response occurs at the level of the microcirculation, and therefore a representative section of skeletal muscle in the leg can be used as the target region. The lumen of the femoral artery may be used as a reference region.

Alphav-beta 5 integrin-targeted microbubbles (Prepared using a peptide targeting ligand using the methods described in Specific Examples 4 and 5) are administered intravenously to a patient suffering from peripheral artery disease during the course of treatment with a pro-angiogenic therapeutic. The leg is imaged using non-destructive ultrasound contrast imaging over 0-6 minutes following microbubble administration. A single field of view, encompassing a representative section of skeletal muscle and the main femoral artery, is acquired and maintained throughout the full imaging duration.

One contrast-mode image is selected at 1 minute and one at 6 minutes following microbubble administration. The images are linearized, and the slope of the reference-scaled contrast signal magnitude between 1 and 6 minutes is computed. This data is used to form a rate image, in which the pixels within the skeletal muscle region are re-colored to represent the magnitude of the reference-scaled contrast signal magnitude slope.

The imaging procedure is repeated periodically during the course of therapy, for example on day −5 (before initiation of treatment), day 5, day 15, day 30, day 60, and day 120.

The series of rate images obtained during the course of treatment are examined in order to ascertain the effectiveness of the therapeutic regimen for the patient. An trend to increase in rate during the treatment, with concomitant increase in the area of the target region exhibiting a positive rate, is considered a positive finding for therapeutic efficacy. The absence of an increasing trend, or of any meaningful regions of the skeletal muscle exhibiting a positive rate at any time during treatment, is considered evidence of failure of the therapy and suggests that alteration of the therapeutic regimen is warranted.

FIG. 18A-E show a simplified example of imaging the response to angiogenic therapy in a patient. The target region (muscle) and reference region (lumen of an adjacent artery) are depicted as a square and circle, respectively. FIGS. 18A and B depict contrast signal magnitude images and corresponding rate image for a patient exhibiting a successful angiogenic response (A) and no angiogenic response (B). In the rate images, all negative rate values are assigned a value of 0, and color mapped to black. Positive rate values are mapped to increasing shades of grey through white.

FIGS. 18 C, D, and E depict a series of rate images obtained at various days during the course of pro-angiogenic therapy. The images represent findings expected for a patient exhibiting a strong response (C), an intermediate response (D), and a poor response (E) to therapy.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for quantifying magnitude of a contrast signal within a region of interest (ROI), the method comprises administering to a target tissue of a subject a targeted contrast agent to image presence of one or more targeted molecular markers of disease; selecting a reference region representative of an amount of the contrast agent circulating within a blood pool in a dynamic scaling, time-varying manner; imaging said target tissue including the selected reference region; determining magnitude quantitatively of an area of disease by said dynamic scaling, time-varying manner procedure wherein said targeted contrast agent is configured to be bound to said one or more molecular markers of disease expressed within a diseased region wherein said dynamic scaling, time-varying manner procedure comprises
   a. providing a time series of images depicting a single field of view,
   b. selecting one or more regions of interest and one or more corresponding reference regions,
   c. forming a reference-scaled image, and/or a reference-scaled signal magnitude in which the region of interest and reference region are obtained at the same instant in the time series,
   d. performing the scaling operation of (c) on two or more images in the time series to determine a time-intensity relationship of the reference-scaled signal magnitude quantitatively; wherein the reference-scaled signal increases in the diseased region and decreases in a non-diseased region.

2. The method of claim 1, comprising scaling the value of each pixel within a dynamically scaled image by a constant.

3. The method of claim 1, wherein the procedure is performed in units of linearized acoustic power or amplitude.

4. The method of claim 1, further comprising color coding of the dynamically scaled images including the images derived from the rates of change of the dynamically scaled images.

5. The method of claim 1, further comprising (a) smoothing by low-pass filtering of the dynamically scaled images, or (b) nonlinear compression of the dynamically scaled images.

6. The method of claim 1, wherein the reference-scaled contrast signal magnitude is computed (a) within one or more target regions at several timepoints between peak signal and clearance of the reference region, or (b) at peak signal and at a subsequent time point of interest, and the average slope between the two points is computed.

7. The method of claim 1, wherein said targeted contrast agent is a microbubble with a mean diameter by number of between 0.1 to 2.0 um, 0.2 to 2.0 um, 0.3 to 2.0 um, 0.4 to 2.0 um, 0.5 to 2.0 um, 0.6 to 2.0 um, or 0.7 to 2.0 um.

8. The method of claim 1, wherein said targeted contrast agent is microbubbles.

9. A method of detecting a disease in a subject comprising imaging a field of view within the subject for between 1-10 minutes and storing the series of images in a readable computer medium; performing the method of claim 1 on the obtained image time series; presenting the scaled image sequence or the scaled signal plot such as a time-intensity curve to a user; and determining a disease based on the rates of change of the scaled signals.

10. The method of claim 9, wherein the field of view comprises a heart, a kidney, a liver, a breast, a tumor, or a prostate.

11. The method of claim 10, wherein the field of view comprises a heart.

12. The method of claim 11, wherein a LV chamber is a reference region, and myocardium is a target region.

13. The method of claim 12, wherein a dynamic scaling procedure is performed on the linearized contrast signal.

14. A dynamic scaling, time-varying manner procedure used to determine the levels of an interested molecular marker configured to be bound to a contrast agent in a target tissue comprises
   a. capturing a series of images of the target tissue over time,
   b. choosing a region of interest within the images that has targeted contrast agent signals, c. choosing a reference region of interest within the images that doesn't have targeted contrast agent signals but has circulating contrast agent signals,
d. using the signal intensities of the reference region to scale the signal magnitudes from the region of interest at each time points;
e. creating reference-scaled images or magnitudes of the target tissue in the different time points, and
f. using the reference-scaled images or magnitudes to determine the levels of the interested molecular marker in the target tissue.

15. The procedure of claim 14, wherein the procedure is performed in units of linearized acoustic power or amplitude.

16. The procedure of claim 14, further comprising (a) color coding of the dynamically scaled images including the images derived from the rates of change of the dynamically scaled images, (b) smoothing by low-pass filtering of the dynamically scaled images, or (c) nonlinear compression of the dynamically scaled images.

17. The procedure of claim 14, wherein the reference scaled signal magnitude is computed (a) within one or more targeted regions at several timepoints between peak signal and clearance of the reference region, or (b) at peak signal and at a subsequent time point of interest, and the average slope between the two points is computed.

* * * * *